United States Patent
Deglon

(10) Patent No.: US 9,695,443 B2
(45) Date of Patent: Jul. 4, 2017

(54) VECTOR FOR THE SELECTIVE SILENCING OF A GENE IN ASTROCYTES

(71) Applicant: Commissariat a l'Energie Atomique et aux Energies Alternatives, Paris (FR)

(72) Inventor: Nicole Deglon, Marseille (CH)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/403,722

(22) PCT Filed: May 24, 2013

(86) PCT No.: PCT/IB2013/054308
§ 371 (c)(1),
(2) Date: Nov. 25, 2014

(87) PCT Pub. No.: WO2013/175446
PCT Pub. Date: Nov. 28, 2013

(65) Prior Publication Data
US 2015/0159171 A1 Jun. 11, 2015

(30) Foreign Application Priority Data

May 25, 2012 (EP) .................................... 12305588
Jul. 10, 2012 (EP) .................................... 12305828

(51) Int. Cl.
*C12N 15/11* (2006.01)
*C12N 15/86* (2006.01)

(52) U.S. Cl.
CPC ............ *C12N 15/86* (2013.01); *C12N 15/111* (2013.01); *C12N 2330/51* (2013.01); *C12N 2740/15033* (2013.01); *C12N 2740/15043* (2013.01); *C12N 2740/15045* (2013.01); *C12N 2740/16033* (2013.01); *C12N 2740/16043* (2013.01); *C12N 2810/6081* (2013.01); *C12N 2830/003* (2013.01); *C12N 2830/205* (2013.01); *C12N 2830/48* (2013.01)

(58) Field of Classification Search
CPC ........................ C12N 15/113; C12N 2310/141
See application file for complete search history.

(56) References Cited

U.S. PATENT DOCUMENTS

2003/0228284 A1* 12/2003 McCown ............. A61K 48/005
424/93.2
2010/0098664 A1    4/2010 Desclaux et al.
2010/0234448 A1*  9/2010 Zamore ................. C12N 15/111
514/44 A
2014/0335054 A1* 11/2014 Gao ....................... C12N 15/86
424/93.2

OTHER PUBLICATIONS

Fahrner et al. Eur. J. Biochem. 213, 1067-1073, 1993.*
Shin et al. The Journal of Cell Biology 2005 171: 1001-1012 and correction.*
Garcia de Veas Lovillo et al. Eur. J. Biochem. 270. 206-212, 2003.*
Colin et al., "Engineered Lentiviral Vector Targeting Astrocytes In Vivo," GLIA, 57: 667-679 (2009).
Faideau et al., "In vivo expression of polyglutamine-expanded hungingtin by mouse striatal astrocytes impairs glutamate transport: a correlation with Huntington's disease subjects," Human Molecular Genetics, 19: 3053-3067 (2010).
Jakobsson et al., "Lentiviral Vectors for Use in the Central Nervous System," Molecular Therapy, 13: 484-493 (2006).
Vigna et al., "Efficient Tet-Dependent Expression of Human Factor IX in Vivo by a New Self-Regulating Lentiviral Vector," Molecular Therapy, 11: 763-775 (2005).
Boudreau et al., "Artificial MicroRNAs as siRNA Shuttles: Improved Safety as Compared to shRNAs In vitro and In vivo," Molecular Therapy, 17: 169-175 (2009).
Thakker et al., "Interfering with the brain: Use of RNA interference for understanding the pathophysiology of psychiatric and neurological disorders," Pharmacology & Therapeutics, 109: 413-438 (2006).
International Search Report issued in corresponding International Patent Application No. PCT/IB2013/054308 dated Sep. 9, 2013.
Written Opinion issued in corresponding International Patent Application No. PCT/IB2013/054308 dated Sep. 9, 2013.

* cited by examiner

*Primary Examiner* — Brian Whiteman
(74) *Attorney, Agent, or Firm* — Morgan, Lewis & Bockius LLP

(57) ABSTRACT

The present invention relates to a viral vector for silencing a gene specifically in astrocytes comprising: —an astrocyte-specific viral envelope protein, —a first nucleic acid sequence encoding a transcription activator and at least one target sequence of a neuron-specific miR under the control of an astrocyte-specific promoter, and—a second nucleic acid sequence encoding a RNA for silencing the gene under the control of a promoter inducible by the transcription activator.

19 Claims, 8 Drawing Sheets

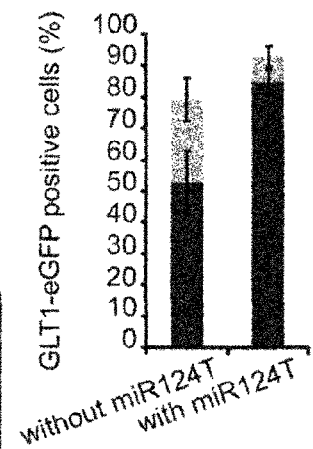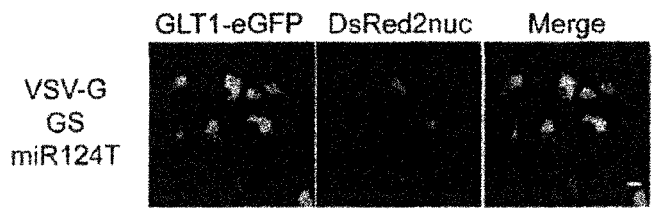
Figure 8A
Figure 8B
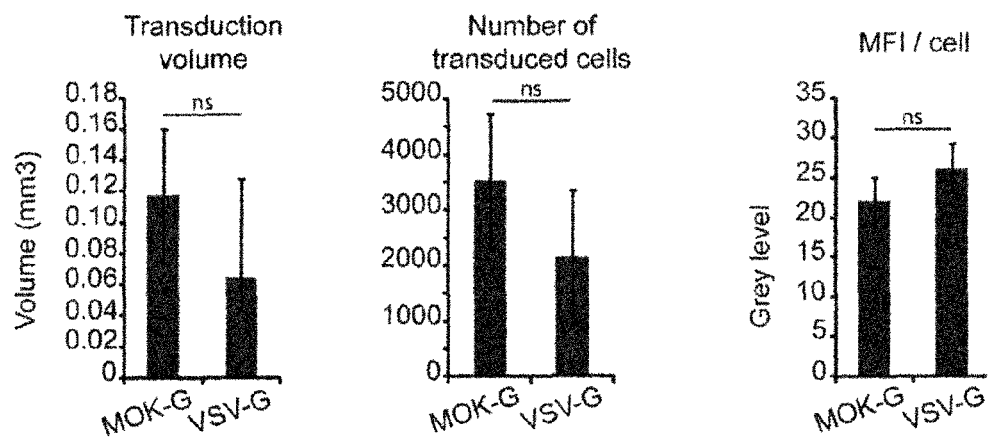
Figure 8C
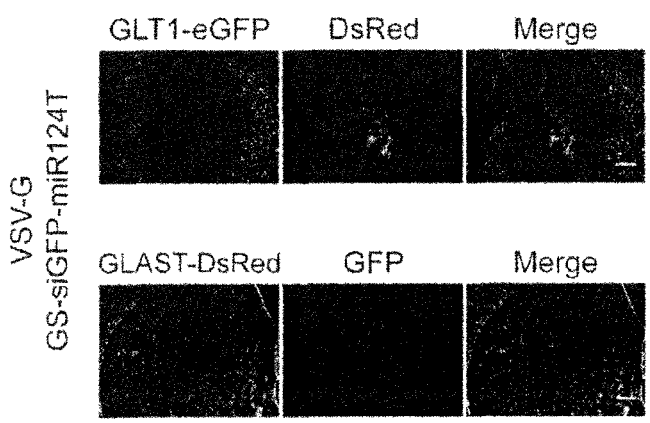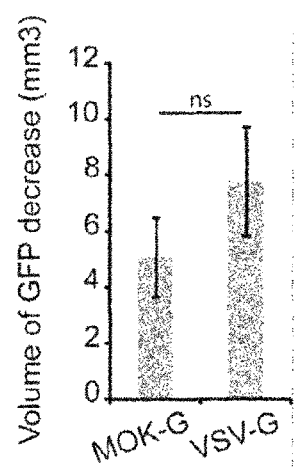
Figure 9A
Figure 9B

VECTOR FOR THE SELECTIVE SILENCING OF A GENE IN ASTROCYTES

SEQUENCE LISTING SUBMISSION VIA EFS-WEB

A computer readable text file, entitled "045636-5268-SequenceListing.txt" created on or about Nov. 18, 2014, with a file size of about 34 kb contains the sequence listing for this application and is hereby incorporated by reference in its entirety.

TECHNICAL FIELD

The present invention relates to a vector for the selective silencing of gene in astrocytes and uses thereof.

TECHNICAL BACKGROUND

Increasing evidences show the importance of astrocytes in the development of neurodegenerative pathologies. In Huntington's disease (HD), neurodegeneration is strongly influenced by the toxicity linked to the production of mutant huntingtin (mHtt) in both neurons and astrocytes. The latter have numerous roles in supporting neurons such as maintaining the blood-brain barrier, regulating the blood flow, the homeostasis of ions and water, the synaptic transmission and the energy metabolism. Nevertheless, the concrete role of astrocytes into neuronal dysfunction and death in HD pathology remains to be determined.

To overexpress a gene specifically in astrocytes, most strategies rely on constitutive or conditional transgene expression in astroglial cells. Among these, one may cite tamoxifen (TAM) inducible CreERT2/loxP system or a constitutive expression of the transgene from an astrocytic promoter such as the GFAP-HD mice model. In these models, the transgene is expressed in astrocytes of almost all brain regions. However, in GFAP-CreERT2-transgenic mice, recombination in neurons is also occurring, since the GFAP promoter is active in embryonic radial glia that possesses a substantial neurogenic potential. In addition, GFAP-driven transgene expression in striatum, the main affected brain area in HD, is very low under physiological conditions. Differences in recombination efficiency between transgenic lines complicate the analysis and it is still not always possible to target specific cell subpopulations through transgenesis. Hence, studying the specific role of astrocytes in HD requires the development of tools specifically targeting this particular cell population in one targeted brain structure.

The development of highly efficient viral vectors for gene transfer in the CNS is providing new systems for localized and controlled gene expression in a subset of cell population (Jakobsson and Lundberg, 2006; Wong et al., 2006). Pseudotyping lentiviral vectors (LVs) with the glycoprotein of the vesicular stomatitis virus (VSV-G) confer a high neurotropism when combined with the ubiquitous promoter of the phosphoglycerate kinase 1 (PGK) (Deglon et al., 2000). In contrast, LVs pseudotyped with the glycoprotein of the Mokola virus (MOK-G) transduce both neurons and glial cells (Cannon et al., 2010; Desmaris et al., 2001; Pertusa et al., 2008; Watson et al., 2002). Furthermore, it has been shown that addition of a micro-RNA target (miRT) restricts transgene expression to cell subpopulations (Brown et al., 2007a; Brown et al., 2007b; Brown et al., 2006). Combining MOK-G pseudotyping with miR124T detargeting is associated with an astrocytic targeting of LVs (Colin et al., 2009). Colin and colleagues have used miR124, which is highly and specifically expressed in neurons (Deo et al., 2006; Lagos-Quintana et al., 2002; Mishima et al., 2007; Smirnova et al., 2005) to overexpress genes of interest into striatal astrocytes in vivo. However, this system is not suitable for silencing a ubiquitous gene because of the maturation of a small interfering RNA (siRNA) by dicer which cleaves the miRT located at the 3'-end of the mRNA and prevents detargeting, as is shown in FIGS. 10A and 10B.

DESCRIPTION OF THE INVENTION

The inventors have now shown that it was possible to overcome this issue and to selectively silence a ubiquitous gene in astrocytes, by combining four methodologies: i) tissue-specific promoters, ii) tetracycline-regulated expression system, iii) miR embedded siRNA expression, and iv) LV pseudotyping.

Thus the present invention relates to a viral vector for silencing a gene specifically in astrocytes comprising:
an astrocyte-specific viral envelope protein,
a first nucleic acid sequence encoding a transcription activator and at least one target sequence of a neuron-specific miR under the control of an astrocyte-specific promoter, and
a second nucleic acid sequence encoding a RNA for silencing the gene under the control of a promoter inducible by the transcription activator.

Advantageously and unexpectedly, the viral vector of the present invention provides for potent silencing of a gene specifically in astrocytes, thus avoiding concomitant silencing in neurons, while in configurations where both the at least one target sequence of a neuron-specific miR and the nucleic acid sequence encoding a RNA for silencing the gene are placed under the control of the same astrocyte-specific promoter a strong silencing is observed in neurons, as is shown in FIGS. 10A and 10B.

As intended herein, "astrocytes" are a sub-type of glial cells, i.e. non neuronal cells, in the central nervous system. They are also known as astrocytic glial cells. Astrocytes are star-shaped and usually express the S100β marker and the Glial Fibrillary Acidic Protein (GFAP).

As intended herein, an "astrocyte-specific viral envelope protein" relates to an envelope protein, in particular an envelope glycoprotein, from a virus which promotes the binding of a vector carrying it, i.e. a vector which is pseudotyped by the envelope protein, to astrocytes. More preferably, an astrocyte-specific viral envelope protein according to the invention promotes a preferential binding of the vector carrying it to astrocytes over at least one cell type other than astrocytes, in particular over neurons.

Preferably, the astrocyte-specific viral envelope protein according to the invention is selected from the group consisting of Mokola virus G protein (G-MOK), rabies G protein, lymphocytic choriomeningitis virus envelope (LCMV), and moloney murine leukemia virus envelope (MuMLV).

More preferably, the astrocyte-specific viral envelope protein according to the invention is Mokola virus G protein (G-MOK).

The "transcription activator" according to the invention is a protein compound which upon binding to a particular locus on the vector will activate the promoter inducible by the transcription activator, which will enable or increase the transcription of the sequence(s) which are controlled by the promoter. As intended herein, the locus may be located next to the promoter or be comprised in the promoter or may be located at distance from the promoter. Numerous transcription activator/promoter inducible by the transcription activator couples according to the invention are known in art.

Preferably, the transcription activator/promoter inducible by the transcription activator according to the invention is selected from the group consisting of a tetracycline transactivator/tetracycline response element (TRE) and a tetracycline transrepressor/tetracycline response element (TRE).

More preferably, the transcription activator according to the invention is the tetracycline transactivator (tTA) and the promoter inducible by the transcription activator is the tetracycline response element (TRE). The tetracycline transactivator is preferably encoded by a sequence comprising or consisting of SEQ ID NO: 1 and the tetracycline response element preferably comprises 7 copies of the tetO operator along with the CMV promoter and is more preferably represented by a sequence comprising or consisting of SEQ ID NO: 2.

As intended herein an "astrocyte-specific promoter" according to the invention relates to a promoter which is constitutively active in astrocytes. More preferably, an astrocyte-specific promoter according to the invention promotes a preferential transcription of sequences within astrocytes over at least one cell type other than astrocytes, in particular over neurons.

Preferably, the astrocyte-specific promoter according to the invention is selected from the group consisting of the promoter of the glutamine synthase (GS) gene, the promoter the human excitatory amino acids transporter 1 (hEAAT1) and the cytomegalovirus (CMV) promoter.

More preferably, the astrocyte-specific promoter according to the invention is the promoter of the glutamine synthase (GS) gene, more preferably the promoter of rat GS gene. The promoter of rat GS gene is preferably represented by a sequence comprising SEQ ID NO: 3.

As intended herein a "neuron-specific miR" according to the invention relates to a microRNA which is present in neurons, in particular in human neurons. More preferably, a neuron-specific miR according to the invention is essentially not expressed in astrocytes. The target sequence of a miR preferably comprises or consists of a sequence complementary to the sequence of the miR.

Preferably, the target sequence of the neuron-specific miR according to the invention is selected from the group consisting of a target sequence of miR124 in particular hsa-miR124, miR128, in particular hsa-miR128, miR10, in particular hsa-miR10 and miR9, in particular hsa-miR9. As will be clear to one of skill in the art "hsa" stands for Homo sapiens.

More preferably, the target sequence of the neuron-specific miR according to the invention is a target sequence of miR124 (miR124T), wherein miR124 most preferably relates to hsa-miR124-3p (SEQ ID NO: 14). miR124T is preferably encoded by a sequence comprising or consisting of SEQ ID NO: 4. More preferably also, the target sequence of the neuron-specific miR according to the invention is a target sequence of miR9 (miR9T), wherein miR9 most preferably relates to hsa-miR9 (SEQ ID NO: 17). miR9T is preferably encoded by a sequence comprising or consisting of SEQ ID NO: 18 or SEQ ID NO: 19.

As will be clear to one of skill in the art, the viral vector of the invention may comprise more than one target sequence of one or more neuron-specific miRs, which may be identical or different. In a preferred embodiment of the invention, the viral vector comprises at least 2, 3, 4, 5, 6, 7, 8, 9 or 10 copies of a same target sequence of a neuron-specific miR according to the invention. In another preferred embodiment of the invention, where the viral vector comprises two or more different target sequences respectively of two or more neuron-specific miRs, the viral vector may comprise at least 2, 3, 4, 5, 6, 7, 8, 9 or 10 copies of each target sequence. In a particularly preferred embodiment of the invention, the viral vector comprises at least one copy of a target sequence of miR124 according to the invention, preferably at least 4 copies of a target sequence of miR124 according to the invention, and at least one copy of a target sequence of miR9 according to the invention, preferably at least 4 copies of a target sequence of miR9 according to the invention. In the latter embodiment, the at least one copy of the miR9 target sequence may either be present in 5' of the at least one copy of the miR124 target sequence, in 3' of the at least one copy of the miR124 target sequence, or mixed with copies of the miR124 target sequence when several copies of the miR124 target sequences are present.

As intended here the RNA for silencing the gene may be of any type known by one of skill in the art. However, it is preferred that it is an antisens RNA, a small interfering RNA (siRNA), or a short hairpin RNA (shRNA), all of which are well known to one of skill in the art and target the mRNA of the gene to silence.

Preferably, the nucleic acid sequence encoding a RNA for silencing the gene according to the invention encodes a siRNA or a shRNA targeting the gene mRNA. More preferably, the shRNA is embedded in a miR sequence, preferably a miR30 sequence. miR–, in particular miR30–, embedding of a shRNA is well known to one of skill in art and notably comprises incorporating the shRNA within the flanking and loop sequences of microRNAs expressed in the cell type wherein expression of shRNA is intended to take place.

As intended herein, a viral vector relate to a particle derived from one or more viruses, in particular by suppression of one or more of its pathogenic or virulence determinants. Preferably, the viral vector according to the invention is selected from the group consisting of lentiviral vectors and adeno-associated vectors.

More preferably, the viral vector according to the invention is a lentiviral vector, most preferably a HIV-1 vector.

Preferably, the first and the second nucleic acid sequences according to the invention are on a same nucleic acid molecule. More preferably, the nucleic acid molecule according to the invention comprises, from 5' to 3':

a 5' long terminal repeat (LTR) sequence, preferably represented by SEQ ID NO: 5, a sequence encoding a siRNA or shRNA targeting the gene, preferably embedded in a miR30 sequence, the GS rat promoter, preferably represented by SEQ ID NO: 3, a sequence encoding the tetracycline transactivator, preferably represented by SEQ ID NO: 1, the woodchuck hepatitis post-transcriptional regulatory element (WPRE), preferably represented by SEQ ID NO: 6, a sequence encoding 4 copies of a miR124 target sequence, preferably represented by SEQ ID NO: 7, and optionally 4 copies of a miR9 target sequence, a 3' long terminal repeat (LTR) sequence, in particular of self-inactivating (SIN) 3' LTR, the tetracycline response element (TRE).

As intended herein, where present, the 4 copies of the miR9 target sequence may either be present in 5' of the 4 copies of the miR124 target sequence, in 3' of the 4 copies of the miR124 target sequence, or mixed with the 4 copies of the miR124 target sequence. Preferably, the 3' long terminal repeat (LTR) sequence, in particular the self-inactivating (SIN) 3' LTR, comprises the tetracycline response element (TRE), and is most preferably represented by SEQ ID NO: 8.

As intended herein, the 5' long terminal repeat (LTR) sequence may be a chimeric LTR sequence comprising a promoter, such as the CMV promoter, as is the case in SEQ ID NO: 5.

Preferably, the gene according to the invention is the huntingtin gene. In that case, the shRNA is preferably encoded by SEQ ID NO: 9 and the miR30-embedded shRNA is preferably encoded by SEQ ID NO: 10.

Thus, most preferably, where the vector is intended for silencing the huntingtin gene, the nucleic acid molecule according to the invention is represented by SEQ ID NO: 11 and the vector is represented by SEQ ID NO: 12.

Preferably, the viral vector according to the invention is for use in the prevention or treatment of astrocyte-mediated diseases.

The present invention also relates to a pharmaceutical composition comprising a viral vector according to the invention as an active ingredient, optionally in association with a pharmaceutically acceptable vehicle or excipient, in particular for use in the prevention or treatment of astrocyte-mediated diseases.

The present invention also relates to a method for preventing or treating astrocyte-mediated diseases in an individual, comprising administering a prophylactically or therapeutically effective amount of a viral vector according to the invention to the individual As intended herein, "astrocyte-mediated diseases" in particular relate to diseases involving a dysfunction of astrocytes, more particularly a dysfunction due to the expression or the over-expression of a protein or glycoprotein. Astrocyte-mediated diseases according to the invention notably encompass Huntington's disease, Parkinson's disease and Alzheimer's disease.

The viral vector according to the invention is preferably formulated as a liquid formulation suitable for injection into the brain. Solutions for preparing a liquid formulation suitable for injection into the brain of a viral vector according to the invention are well known to one of skill in the art and notably comprise the TSSM formulation: 20 mM Trometh-amine, 100 mM NaCl, 10 mg/ml sucrose and 10 mg/ml mannitol.

Viral vector administration may be performed by direct injection into the brain, for instance in the striatum. The viral vector is preferably administered at a dose of from $1 \times 10^5$ transducing units (TU) to $5 \times 10^6$ TU.

The present invention also relates to a method, in particular an in vitro method, for silencing a gene in astrocytes, comprising contacting a viral vector according to the invention with at least one astrocyte.

The present invention also relates to a nucleic acid molecule comprising from 5' to 3':
- a 5' long terminal repeat (LTR) sequence, preferably represented by SEQ ID NO: 5,
- a sequence comprising from 4 to 1000 nucleotides, such as a multiple cloning site or a sequence encoding a siRNA or a shRNA, preferably embedded in a miR30 sequence,
- the GS rat promoter, preferably represented by SEQ ID NO: 3,
- a sequence encoding the tetracycline transactivator, preferably represented by SEQ ID NO: 1,
- the woodchuck hepatitis post-transcriptional regulatory element (WPRE), preferably represented by SEQ ID NO: 6,
- a sequence encoding 4 copies of a miR124 target sequence, preferably represented by SEQ ID NO: 7, and optionally 4 copies of a miR9 target sequence,
- a 3'long terminal repeat (LTR) sequence, in particular a self-inactivating (SIN) 3' LTR,
- the tetracycline response element (TRE)

As intended herein, where present the 4 copies of the miR9 target sequence may either be present in 5' of the 4 copies of the miR124 target sequence, in 3' of the 4 copies of the miR124 target sequence, or mixed with the 4 copies of the miR124 target sequence.

Preferably, the 3'long terminal repeat (LTR) sequence, in particular the self-inactivating (SIN) 3' LTR, comprises the tetracycline response element (TRE), and is most preferably represented by SEQ ID NO: 8.

As intended herein, the 5' long terminal repeat (LTR) sequence may be a chimeric LTR sequence comprising a promoter, such as the CMV promoter, as is the case in SEQ ID NO: 5.

Preferably, where it comprises a multiple cloning site, comprising the SphI and the EcoRV restrictions sites, the nucleic acid molecule according to the invention is represented by SEQ ID NO: 13.

The present invention will now be further described by the following non-limiting Example and figures.

DESCRIPTION OF THE FIGURES

FIG. 1A) MOK-G pseudotyped LVs carrying either CMVa, GFA-ABC1D, EAAT1 or GS were injected into striatum of BAC-GLT1-eGFP mice. Acquisition parameters were optimized for each promoter. FIG. 1B) Quantification of DsRednuc-eGFP- and DsRednuc-NeuN-positive cells shows the astrocytic tropism of all vectors. Scale bar=10 μm.

FIG. 2A) Double immunofluorescence staining for GLT1-eGFP and DsRednuc after the injection of MOK-G pseudotyped LVs into striatum of BAC-GLT1-eGFP. Acquisition parameters were optimized for each promoter. FIG. 2B) Quantification of DsRednuc-eGFP- and DsRednuc-NeuN-positive cells shows the improvement of the astrocytic tropism for all vectors. Scale bar=10 μm.

FIG. 4A) To assess the tropism of the astro-silencing construct, a nuclear-localized GFP (AcGFPnuc) was used. MOK-G pseudotyped LVs were injected into striatum of BAC-GLAST-DsRed mice. As internal promoters, CMVb and GS were used. As control, a LV miR124T-less and containing CMVb was used. FIG. 4B) Quantification of AcGFPnuc-DsRed-, AcGFPnuc-S100β-, AcGFPnuc-NeuN-positive cells shows a tropism preferentially astrocytic with CMVb-miR124T and GS-miR124T. FIG. 4C) Measurement of the mean fluorescence intensity per cell (MFI/cell) highlights the astrocytic activity of GS compared to the ubiquitous CMVb.

FIG. 5A) Typical aspect of striatum BAC-GLT1-eGFP mice injected with PBS. FIG. 5B) GS-siUNIV-miR124T and GS-siGFP-miR124T LVs have been injected into BAC-GLT1-eGFP striatum mice. To localize the injection site, BFP or DsRed have been co-injected with siUNIV and siGFP respectively. Injection of GS-siUNIV-miR124T induced a GFP decrease in the vicinity of BFP whereas injection of GS-siGFP-miR124T induced a large GFP decrease. FIG. 5C) The measurement of the GFP decrease volume shows a significant difference between siGFP and siUNIV, confirming the efficacy of the siGFP. FIG. 5D) GS-siGFP-miR124T LV has also been injected into BAC-GLAST-DsRed striatum mice to confirm that siGFP does not act on promoter to silence the transgene. Scale bar=200 µm.

FIG. 6A) Bicistronic vector encoding Cherry and GFP under the control of CMV minimal and PGK promoters, respectively. This LV has been pseudotyped with VSV-G in order to transduce only neurons. FIG. 6B) Quantification of Green/Red ratio reflects the silencing of GFP. LV-siUNIV (first column) is the internal control and represents the basal level of Green/Red ratio. As a control of the system efficiency, we have used a VSV-G pseudotyped LV encoding the siGFP under the control of the CMVb (third column) in order to target neurons. A significant Green/Red ratio is then observable. When the astro-silencing construct is used (second column), a slight decrease of Green/Red ratio is also observable, reflecting a low tropism for neurons.

FIG. 7A) Double immunofluorescence staining for GLT1-eGFP and DsRed-nuc after the injection of VSV-G pseudotyped LVs into striatum of BAC-GLT1-eGFP. Acquisition parameters were optimized for each promoter. FIG. 7B) Quantification of DsRednuc-eGFP-positive cells shows a partial astrocytic tropism with VSV-G pseudotyped LVs with CMVa or GS. Scale bar=10 µm.

FIGS. 8A, 8B and 8C: Tropism of lentiviral vectors with a VSV-G envelope and GS promoter combining with miR124T. FIG. 8A) Double immunofluorescence staining for GLT1-eGFP and DsRednuc after the injection of VSV-G pseudotyped LV GS-DsRednuc-miR124T into striatum of BAC-GLT1-eGFP. FIG. 8B) Quantification of DsRednuc-eGFP- and DsRednuc-NeuN-positive cells shows an astrocytic tropism with miR124T compared to LV without miR124T. Scale bar=10 µm. FIG. 8C) Comparison of LVs characteristics (i.e. transduction volume, number of transduced cells and MFI/cell) when pseudotyped by either MOK-G or VSV-G highlights no significant differences.

FIGS. 9A and 9B: Validation of the astro-silencing construct with a VSV-G envelope. FIG. 9A) GS-siGFP-miR124T LV pseudotyped with VSV-G has been injected into BAC-GLT1-eGFP and BAC-GLAST-DsRed striatum mice; to localize the injection site, DsRed or GFP have been co-injected respectively. FIG. 9B) The measurement of the GFP decrease volume shows no significant difference between the two envelopes, MOK-G and VSV-G. Scale bar=200 µm.

FIG. 10A) The integration of miRT sequence at the 3' end of a PGK-miR30-siGFP expression cassette (siGFP-miR124T) is not efficacious for a cell-type specific silencing since a silencing (Volume of GFP silencing (mm$^3$) vertical axis) non significantly (NS) different from that directed by the PGK-miR30-siGFP alone (siGFP) is obtained in the brain of mice injected with lentiviral vectors containing the cassettes (siUNIV and PBS: negative controls). FIG. 10B) The latter observation is due to the cleavage by dicer of the miR124T detargeting sequence during the processing of the miR30-embedded siGFP, which prevents the miR124-mediated destruction of the transcript harboring siGFP in neurons.

EXAMPLE

Figure 1A:
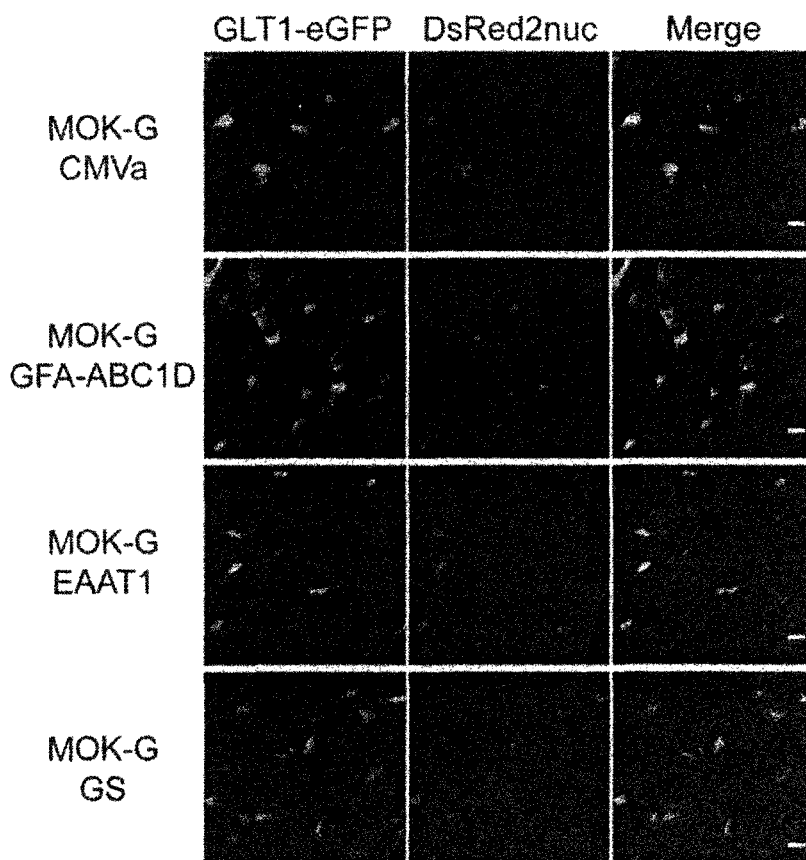
FIGS. 1A and 1B: Transduction efficiency and tropism in adult mice of lentiviral vectors containing the astrocytic promoters.

In the present experimental setting, the tissue-specific promoter is driving the expression of the tetracycline trans-activation and the miRT is further restricting the expression of the siRNA in astrocytes.

As tissue-specific promoters, the inventors have analysed three astrocytic promoters: the one of the excitatory amino acid transporter 1 (EAAT1), the glutamine synthetase (GS) and the shortest form of the GFAP promoter (GFA-ABC1D). These promoters were first tested in a constitutive system and then integrated in a single regulated vector previously described (Vigna et al., 2005). Recent studies have demonstrated that siRNA embedded in a miRNA backbone may provide safer therapeutic for siRNA expression vectors, as compared to small hairpin RNAs, by decreasing the risk of saturation of the endogenous siRNA machinery (Boudreau et al., 2009). In addition pol II promoters, such as tissue-specific promoters, are used to express miR-embedded siRNA (Boudreau et al., 2009; Boudreau et al., 2008; McBride et al., 2008). As a proof-of-principle, the inventors have used a siRNA directed against the green fluorescent protein (GFP) reporter gene (siGFP). This siGFP has been embedded in miR30 (Boudreau et al., 2009; McBride et al., 2008); the design is such that the final mature siRNA is identical to the original H1-shRNA cassette (Boudreau et al., 2008). Finally, the inventors have compared VSV-G and MOK-G envelopes to target astrocytes when combined with a tissue-specific promoter and with or without the miR124T sequence. To facilitate the analysis, BAC-GLT1-eGFP mice, which express GFP exclusively in astrocytes (GLT1 is specific of astrocytes) have been used (Regan et al., 2007).

Materials and Methods

Plasmids

For the tissue-specificity study, the inventors used self-inactivated (SIN) lentiviral vectors (LV) (Deglon et al., 2000) containing the woodchuck post-regulatory element (WPRE, W), encoding the nuclear-localized red fluorescent protein (pDsRed2-Nuc, Clontech, Saint-Germain-en-Laye, France) and with or without 4 copies of the synthetic target of the miR124 (miR124T coding sequence: TGGCAT-TCACCGCGTGCCTTA (SEQ ID NO: 4); SIN-W-DsRed2nuc and SIN-W-DsRed2nuc-miR124T).

The following internal promoters were used: the ubiquitous mouse phosphoglycerate kinase 1 promoter (PGK; from −430 to +74 relative to the transcriptional start site (TSS); GenBank M18735.1 nt: 423 to 931) (Adra et al., 1987; Deglon et al., 2000) and the human cytomegalovirus (688 bp CMVa from pcDNA3.1 plasmid, Clontech, Saint-Germain-en-Laye, France; GenBank K03104, nt: 137 to 723 and sequences with a putative transcriptional start site, T7 primer binding site and multiple cloning sites). A slightly different fragment of the human cytomegalovirus promoter was cloned in the inducible vector (606 bp CMVb; GenBank K03104, nt: 207 to 791).

The following promoters the inventors used for tissue-specific expression: the 2 kb human excitatory amino acid transporter 1 (EAAT1; synthesized by GeneArt (Invitrogen, Cergy-Pontoise, France; GenBank AF448436.1, nt: 1 to 2051) promoter (Kim et al., 2003); the shortest form, 681 pb, of the human glial fibrillary acidic protein (pGFA-ABC1D; courtesy of Dr Brenner, Birmingham, USA; GenBank NG_008401.1, nt: 3292 to 3793 and 4916 to 5094) promoter (Lee et al., 2008); and the 432 pb rat glutamine synthetase (GS; GenBank M91651.1, nt: 2111 to 2543) promoter which was amplified from rat genomic DNA with the following primers: 5'-CACCATCGATGGCTCGCTCAACAAAGGG-TAA-3' (SEQ ID NO: 15) and 5'-GGATCCCTCGGCT-GTGGAGGGTTGCGG-3' (SEQ ID NO: 16) (GenBank M91651.1, nt: 1 to 2132 with a CACC flanking sequence for oriented cloning—and nt: 2524 to 2543 for forward and reverse primer, respectively) (Mill et al., 1991).

For the silencing study, the inventors used a one-single inducible system (courtesy of Prof Naldini, Milano, Italy) (Vigna et al., 2005), self-inactivated LV with an internal cytomegalovirus promoter (pCCL) and containing: i) the transactivator sequence (tTA/S2), ii) the tetracycline response element (TRE), iii) the central polypurine tract (cPPT), iv) the GS promoter or the human cytomegalovirus promoter (CMVb; GenBank AY468486.1, nt: 2020 to 2624), v) the WPRE, vi) four copies of miR124T, and vii) a multiple cloning site (MCS) (pCCL-MCS-cPPT-GS-tTA/S2-W-miR124T-TRE-SIN). To assess the tissue-specificity of such a vector, they first cloned the nuclear-localized green fluorescent protein (pAcGFP1-Nuc; Clontech, Saint-Germain-en-Laye, France) by a NheI restriction enzyme digestion into the MCS (pCCL-AcGFPnuc-cPPT-GS-tTA/S2-W-miR124T-TRE-SIN). To evaluate the silencing potential of the vector, the inventors used an siRNA directed against the green fluorescent protein (siGFP; Drouet et al. 2009) and as control a siRNA with no sequence homology in the genome (siUNIV). These siRNAs were embedded in a miR30 5' and 3' flanking regions and synthesized by GeneArt (Invitrogen, Cergy-Pontoise, France). A SacI-KpnI fragment was excised from the pENTR plasmid, end-filled with T4 DNA polymerase (Invitrogen, Cergy-Pontoise, France) and inserted as a blunt-ended fragment into the destination plasmid (pCCL-miR30-siRNA-cPPT-GS-tTA/S2-W-miR124T-TRE-SIN).

To localize the injection site, the inventors used LVs expressing reporter genes under the control of the mouse PGK: either the DsRed (SIN-W-PGK-DsRed) or the blue fluorescent protein (BFP, SIN-W-PGK-BFP).

To evaluate the specificity of our silencing contructs, the inventors used a bicistronic vector (pCCL-mCherry-CMVmin-hPGK-eGFP-WPRE-SIN; courtesy of Prof Naldini, Milano, Italy) containing: i) the red fluorescent protein (Cherry) reporter gene under the control of a minimal CMV promoter, ii) the GFP reporter gene under the control of the mouse PGK promoter, iii) the WPRE, and iv) an unidirectional polyA signal derived from the SV40. This LV encodes both Cherry and GFP.

Lentiviral Vector Production

Lentiviral vectors were produced in 293T cells, using a four-plasmid system, as previously described (Hottinger et al., 2000). The HIV-1 vectors were pseudotyped with either the vesicular stomatitis virus G protein (VSV-G) or a codon-optimized version of the G protein of Mokola lyssavirus (MOK-G) (pMOK-G; GeneArt). Viruses were concentrated by ultracentrifugation and resuspended in phosphate-buffered saline (PBS)/1% bovine serum albumin (BSA). The viral particle content of each batch was determined by p24 antigen enzyme-linked immunosorbent assay (RETROtek; Gentaur, Paris, France). The stocks were stored at −80° C. until use.

Animals

Male C57BL/6 mice (weight, 20 g; Iffa Credo/Charles River, France) and adult transgenic mice (BAC-GLT1-eGFP and BAC-GLAST-DsRed) (weight, around 20-25 g; lineage perpetrated in our own animal house) (Regan et al., 2007) were used. The animals were housed in a temperature-controlled room and maintained on a 12 h day/night cycle. Food and water were available ad libitum. All experimental procedures were performed in strict accordance with the recommendations of the European Community directive (86/609/EEC) concerning the care and use of laboratory animals.

Stereotaxic Injections

Tissue-Specificity Study

Concentrated viral stocks were thawed on ice and resuspended by vortexing and repeated pipetting. SIN-W-promoter-DsRed2nuc LVs with or without the miR124T were diluted in PBS/1% BSA to a final concentration of 67 ng p24/µl. BAC-GLT1-eGFP mice were anesthetized by intraperitoneal injection with a mixture of 150 mg/kg ketamine and 10 mg/kg xylazine (Coveto, Montaigu, France). Suspensions of lentiviral vectors were injected into the brain using a 34-gauge blunt-tip needle linked to a Hamilton syringe by a polyethylene catheter. Stereotaxic coordinates for injection into mouse striatum were, from bregma: antero-posterior +1 mm; lateral +/−2 mm and ventral −2.5 mm from the dura, with tooth bar set at 0 mm (Franklin and Paxinos, 1997). Mice received a total volume of 3 µl of the vector preparation, administered at a rate of 0.2 µl/min. At the end of injections, needles were left in place for 5 min before being slowly removed. The skin was sutured and mice were allowed to recover.

Silencing Study

To assess the tropism of the silencing vector, pCCL-AcGFPnuc-cPPT-GS-tTA/S2-W-miR124T-TRE-SIN was diluted in PBS/1% BSA to a final concentration of 67 ng p24/µl. BAC-GLAST-DsRed mice were anesthetized by intraperitoneal injection with a mixture of 150 mg/kg ketamine and 10 mg/kg xylazine (Coveto, Montaigu, France). Suspensions of lentiviral vectors were injected into the brain using a 34-gauge blunt-tip needle linked to a Hamilton syringe by a polyethylene catheter. Stereotaxic coordinates for injection into mouse striatum were, from bregma: antero-posterior +1 mm; lateral +/−2 mm and ventral −2.5 mm from the dura, with tooth bar set at 0 mm (Franklin and Paxinos, 1997). Mice received a total volume of 3 µl of the vector preparation, administered at a rate of 0.2 µl/min. At the end of injections, needles were left in place for 5 min before being slowly removed. The skin was sutured and mice were allowed to recover.

For evaluating the specificity of the silencing vector, the bicistronic LV was diluted in PBS/1% BSA to a final concentration of 33 ng p24/µl. C57BL/6 mice were anesthetized and injected as described above. Mice received a total volume of 3 µl of the vector preparation, administered at a rate of 0.2 µl/min. At the end of injections, needles were left in place for 5 min before being slowly removed. The skin was sutured and mice were allowed to recover.

For the silencing, pCCL-miR30-siGFP or miR30-siUNIV-cPPT-GS-tTA/S2-W-miR124T-TRE-SIN were diluted in PBS/1% BSA to a final concentration of 67 ng p24/µl; localization LVs SIN-W-PGK-DsRed and SIN-W-

PGK-BFP were diluted to a final concentration of 17 ng p24/μl. BAC-GLT1-eGFP mice were anesthetized and injected as described above. Mice received a total volume of 3 μl of the vector preparation, administered at a rate of 0.2 μl/min. At the end of injections, needles were left in place for 5 min before being slowly removed. The skin was sutured and mice were allowed to recover.

Histological Processing

Tissue Preparation

Two (silencing study) or three weeks (tissue-specificity study) post-lentiviral injection, the animals were killed with an overdose of sodium pentobarbital and transcardially perfused with a 4% paraformaldehyde (PFA; Sigma-Aldrich, Saint-Quentin Fallavier, France) solution. The brains were removed and post-fixed by incubation in 4% PFA for about 12 h and then cryoprotected first in 15% sucrose/0.1 M PBS overnight and then in 30% sucrose/0.1 M PBS for 24 h. A sledge microtome with a freezing stage at −30° C. (SM2400; Leica, Nanterre, France) was used to cut brain coronal sections 30 μm thick. Slices throughout the entire striatum were collected and stored in tubes as free-floating sections in PBS supplemented with 0.14M sodium azide. Tubes were stored at 4° C. until immunohistochemical processing.

Primary Antibodies

The following primary antibodies were used: mouse monoclonal anti-neuronal nuclei antibody (NeuN, dilution 1/200; MAB377, Millipore, Molsheim, France); mouse monoclonal antibody recognizing the β subunit of the S100 protein (S100β, dilution 1/500; S2532, Sigma-Aldrich, Saint-Quentin Fallavier, France).

Immunohistochemical Procedure

For the tissue-specificity study and the silencing study, one serial was mounted directly in an aqueous medium (FluorSave, Life Technologies, Saint Aubin, France).

For the study of SIN-W-promoter-DsRed±miR124T tropism, sections from BAC-GLT1-eGFP mice were labeled with NeuN antibody. Staining was performed with the mouse-on-mouse detection kit Vector® M.O.M. kit (Basic) (Clinisciences, Nanterre, France). As secondary antibody, the AlexaFluor 350 (blue) anti-mouse diluted 1/500 (Life Technologies, Saint Aubin, France) was used.

For the tropism of pCCL-AcGFPnuc-cPPT-GS-tTA/S2-W-miR124T-TRE-SIN, two serials from BAC-GLAST-DsRed mice were labeled with either NeuN or S100β antibodies also by using the basic M.O.M. kit (Clinisciences, Nanterre, France). As secondary antibody, the AlexaFluor 350 (blue) anti-mouse diluted 1/500 (Life Technologies, Saint Aubin, France) was used.

Quantitative Analysis

Co-Localization with Astrocytic or Neuronal Markers

Sections labeled for GLT1-eGFP, NeuN or S100β were analyzed by epifluorescence microscopy with a Leica DM6000B (Leica, Nanterre, France) microscope equipped with an automated motorized stage and image acquisition software (MorphoStrider, Explora nova, La Rochelle, France).

For the tissue-specificity study, the numbers of DsRed2nuc-NeuN-positive cells and DsRed2nuc-GLT1-eGFP-positive cells were determined on images acquired with a 40× objective (six animals, three sections per animal, six images per section) by ImageJ software (rsb.info.nih.gov/ij/).

To assess the tropism of pCCL-AcGFPnuc-cPPT-GS-tTA/S2-W-miR124T-TRE-SIN, the numbers of AcGFPnuc-NeuN-positive cells and AcGFPnuc-S10013-positive or AcGFPnuc-GLAST-DsRed-positive cells were determined on images acquired with a 40× objective (six animals, three sections per animal, six images per section) by ImageJ software (rsb.info.nih.gov/ij/).

Mean Fluorescence Intensity Per Cell

For the silencing study, to quantify the mean fluorescence intensity per cell (MFI/cell) in neurons and in astrocytes, photomicrographs of AcGFPnuc-positive BAC-GLAST-DsRed mice sections, stained with NeuN or S100β, were acquired with a 40× objective (Morphostrider software; Explora Nova, La Rochelle, France). The acquisition parameters of the Leica DM6000B microscope (excitation neutral attenuator filters and obturator) were maintained equivalent for all acquisitions while camera parameters (time of exposure from 300 to 900 ms, and gain from 1 to 3) were adjusted for each group (e.g. pCCL-AcGFPnuc-cPPT-GS-tTA/S2-W-miR124T-TRE-S1N and pCCL-AcGFPnuc-cPPT-CMVb-tTA/S2-W-miR124T-TRE-SIN) to maximize fluorescence but without saturation (avoided using display of pixel fluorescence intensity histogram). Co-localization with NeuN or S100β was used to delimit the neurons (70 on average for each group) and the astrocytes (400 in average for each group) and the ImageJ software automatically calculated the mean gray level of the various objects drawn. To allow semi-quantitative comparison between the constructs, fluorescence levels for each group (construct) was normalized to the same time exposure (500 ms, gain 1). The inventors experimentally checked that fluorescence emission (gray levels) GFP containing brain sections was linearly proportional to exposure time in the range they used (300-900 ms) and for the different gains used.

For the comparison of VSV-G and MOK-G envelopes with SIN-W-GS-DsRed2nuc-miR124T, photomicrographs of DsRednuc-positive BAC-GLT1-eGFP mice sections were acquired with a 10× objective. Mosaic pictures covering the entire striatum were generated (Morphostrider software; Explora Nova, La Rochelle, France) and used to measure the fluorescence intensity. The acquisition parameters of the Leica DM6000B microscope (excitation neutral attenuator filters and obturator) were maintained equivalent for all acquisitions as the camera parameters. The section closest to the injection site was used to measure the MFI/cell. The DsRednuc-positive area was delimited and a gray level threshold was applied for automated segmentation and count of infected cells expressing GFP (the lower limit of the gray level was set-up at 9). The ImageJ software automatically calculated the number of transduced cells and the mean gray level of the various objects identified. To determine the transduction volume, DsRednuc-positive area was delimited for each section and the volume calculated based on this data as we know that at 10× objective, 1 pixel represents 0.643299 μm.

To measure the silencing level in neurons with the bicistronic vector, photomicrographs of the GFP-Cherry-positive C57BL/6 mice sections were acquired with a 10× objective. Mosaic pictures covering the entire striatum were generated (Morphostrider software; Explora Nova, La Rochelle, France) and used to measure the fluorescence intensity for each reporter gene. The acquisition parameters of the Leica DM6000B microscope (excitation neutral attenuator filters and obturator) were maintained equivalent for all acquisitions as the camera parameters. GFP-positive and Cherry-positive areas were delimited and the mean fluorescence intensity automatically calculated (Mercator software; Explora Nova, La Rochelle, France). Green/Red ratio was then calculated.

Statistical Analysis

Data were analyzed using GraphPad Prism 4 Software (GraphPad Software, La Jolla, USA). A paired t test analysis was used to evaluate the significance differences of MFI/neuron vs MFI/astrocyte (set at P<0.05). Unpaired t test analysis were used to appraise the significance differences of the volume of GFP decrease (siUNIV vs siGFP and VSV-G vs MOK-G) in the silencing study and to compare the features of VSV-G and MOK-G pseudotyped LVs (set at P<0.05). One-way ANOVA with a post-hoc Newman-Keuls test analysis was used to assess the significance of differences (set at P<0.05) for the study of specificity based on the use of the bicistronic vector. Data are presented as means±standard error of the mean (SEM).

Results

Effect of Astrocytic Promoters on LVs Tropism

Figure 1B:
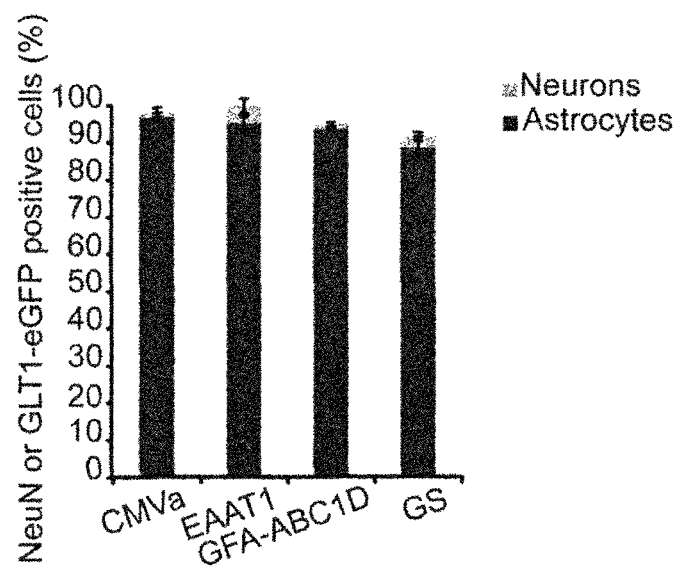

As a first step toward the establishment of an astrocyte-specific silencing, the inventors evaluate three astrocytic promoters. The human glial fibrillary acidic protein (GFAP), the human excitatory amino acid transporter 1 (EAAT1) and the rat glutamine synthetase (GS) were cloned upstream of a nuclear DsRed (SIN-W-DsRed2nuc) and pseudotyped with the MOK-G envelope. As controls, LVs with the housekeeping PGK and CMVa promoters (SIN-W-PGK/CMVa-DsRed2nuc) and a VSV-G envelope were used (Deglon et al., 2000). The constructs were injected into striatum of adult BAC-GLT1-eGFP mice, and three weeks later the mice were sacrificed and sections of the striatum were processed for immunofluorescence. DsRed was detected in nuclei around the injection site in all animals; no fluorescence was detected in the untreated contralateral striatum. Antibody against the neuronal marker NeuN and the endogenous GLT1-eGFP, expressed only in astrocytes, were used to determine the phenotype of the transduced cells (FIG. 1). Microscopic analysis and cell counts revealed that for all astrocytic promoters, more than 90% of the transduced cells co-localized with GLT1-eGFP, whereas only scarce DsRed2nuc-positive cells were double-stained for NeuN (FIG. 1). Thus, all these promoters retained an astrocytic specificity. Interestingly, CMVa leads to the same results as observed with astrocytic promoters, confirming its transcriptional pattern to be more astrocytic than PGK: 92% of DsRed-positive cells were astrocytes on average, 96.4±1.1% for CMVa and only 62.9±2.7% for PGK. LV PGK specifically targets neurons with more than 90% of co-localization with the marker NeuN; whereas, pseudotyping with a MOK-G envelope shifts the tropism of the LV-PGK-DsRed2nuc with more than 70% of transduced cells co-localizing with GLT1-eGFP-positive astrocytes.

Figure 2A:
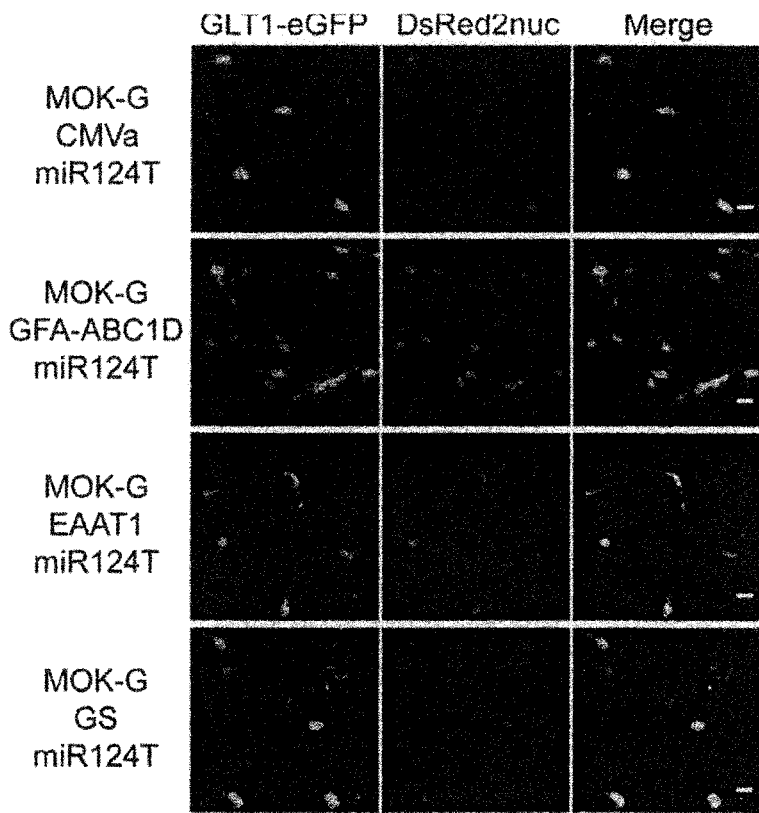
FIGS. 2A and 2B: Combinatorial effect of MOK-G and miR124T on lentiviral vectors tropism with astrocytic promoters.
Figure 2B:
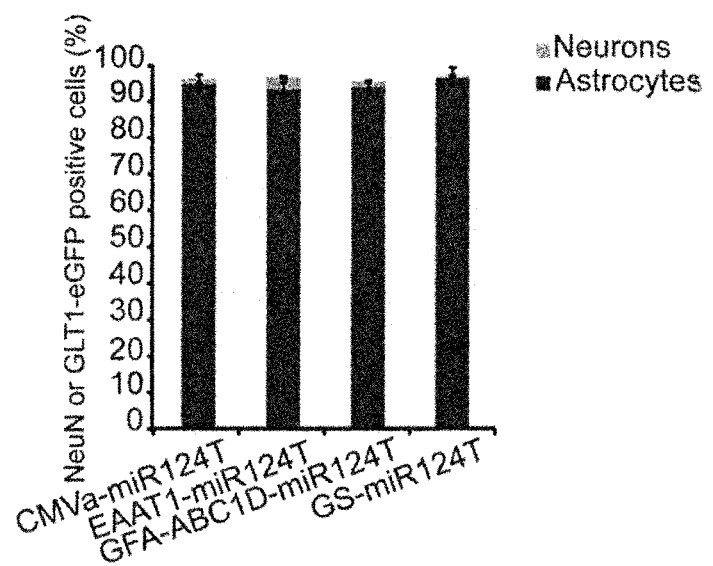

Effect of the Combination of an Astrocytic Promoter with the miR124T Detargeting Strategy on LVs Tropism To further improve the selectivity of the transgene expression, the inventors then used a detargeting strategy based on the addition of four copies of a synthetic miR124T sequence after the transgene. CMVa, EAAT1, GFA-ABC1D and GS promoters were inserted into SIN-W-DsRed2nuc-miR124T LVs and pseudotyped with MOK-G. The constructs were administered by injection into striatum of adult BAC-GLT1-eGFP mice. Three weeks later, mice were sacrificed and sections of the striatum were double-stained with the marker NeuN for co-localization analysis. Quantification of this co-localization between DsRed2nuc and either GLT1-eGFP or NeuN revealed a strong astrocytic tropism for all LVs tested: around 95% of DsRed2nuc positive cells were GLT1-eGFP-positive (FIG. 2). In particular, for GS promoter, there is a great improvement in targeting astrocytes by addition of the miR124T compared to LVs without miR124T (96.3±2.5% and 88.2±2.9%, respectively) (FIG. 1 and FIG. 2). Based on those results, we have chosen to pursue the studies with the GS promoter.

Construction and Tropism of the Astro-Silencing Lentiviral Vector

Figure 3:
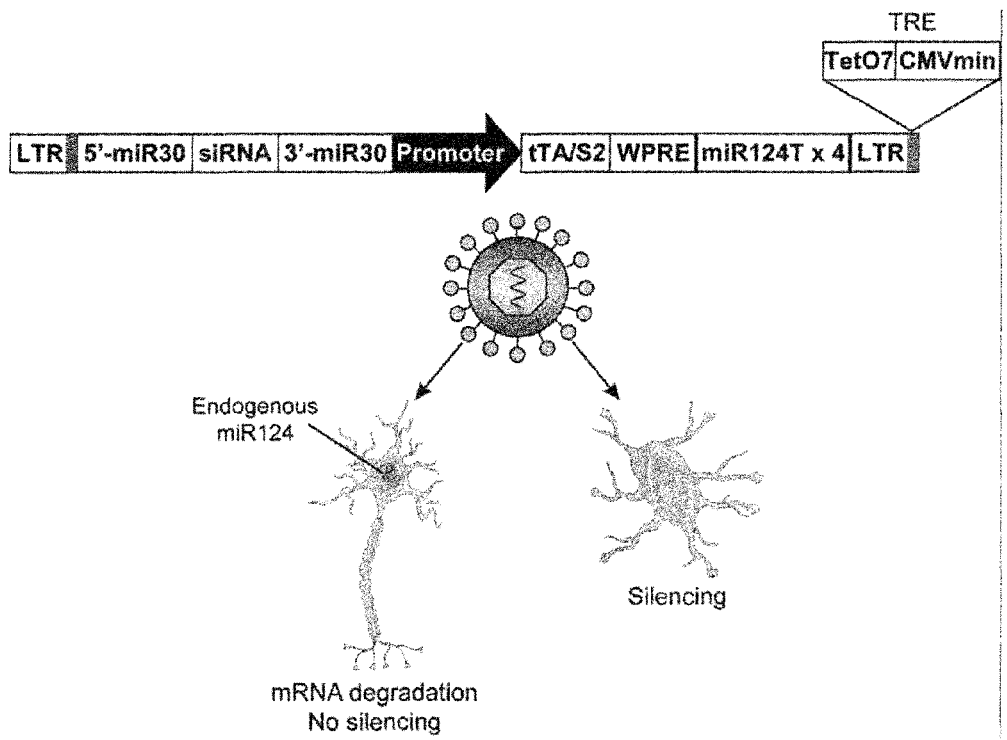
FIG. 3: Principle of the astro-silencing lentiviral vector. The schema represents the different elements composing the astro-silencing vector based on the use of the tetracycline-regulated system. If the LV enters into a neuron, the binding of miR124 to its target leads to the degradation of the mRNA, preventing for silencing. However, as astrocytes do not contain miR124, there is no mRNA degradation. Hence, theoretically, silencing should be observed only in astrocytes.

The next step in the development of an astrocyte-specific silencing was the integration of all these elements in a single tetracycline-regulated lentiviral backbone (Vigna et al., 2005) (FIG. 3). Briefly, the strategy is based on the integration of four copies of the miR124T sequence on the 3'-end of the transactivator (tTA/S2) mRNA in order to prevent neuronal expression of the transgene. Moreover, to ensure an astrocytic expression, the tTA/S2-miR124T cassette is under the control of an astrocytic promoter. Hence, if LV enters into neurons, mRNA corresponding to tTA/S2-miR124T is degraded whereas if LV enters into astrocytes, there is no degradation and tTA/S2 binds to the tetracycline response element (TRE) and activate the CMV minimal promoter.

Figure 4A:
FIGS. 4A, 4B and 4C: Tropism of the astro-silencing lentiviral vector.
Figure 4B:
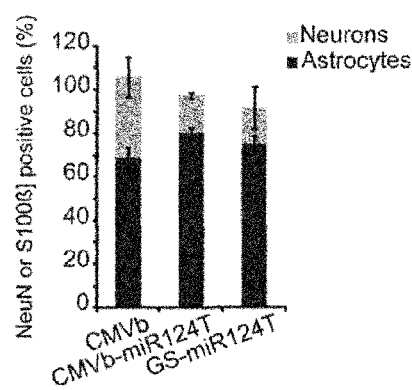

Based on previous results, the inventors have placed tTA/S2 under the control of either the GS promoter or CMVb as control (FIG. 4) and added four copies of the miR124T. The tropism of LVs was assessed with a nuclear GFP (AcGFPnuc) reporter gene. The vectors were pseudotyped with MOK-G and injected into striatum of adult BAC-GLAST-DsRed mice. Quantitative analysis of NeuN- and S100β-positive cells three weeks post-injection in the striatum confirmed the importance of the presence of miR124T with 69±4.6% for CMVb against 80.3±2.3% for CMVb-miR124T of double-stained astrocytes (FIG. 4B). With GS promoter combined with miR124T, 75.2±3.5% of astrocytes are transduced (FIG. 4B).

Figure 4C:
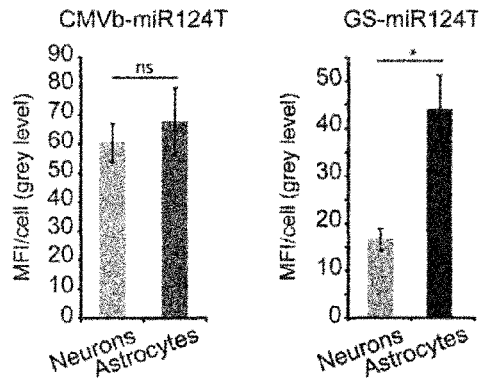

To further quantify the residual transcriptional activity in neurons, the mean fluorescence intensity per cell (MFI/cell) was measured. The inventors show that with the GS promoter, a lower MFI/cell was observed in neurons compared with astrocytes (16.6±2.3 vs 44.2±7.1 grey level, respectively; P=0.0347, paired t test) (FIG. 4C) whereas with the CMVb, there was no significant difference in transcriptional activity between neurons and astrocytes (60.6±6.7 vs 68.0±11.5 grey level, respectively; P=0.0885, paired t test) (FIG. 4C). Hence, it confirms the interest of the GS promoter in this configuration.

Validation of the Astro-Silencing Construct with a siGFP

Figure 5A:
FIGS. 5A, 5B, 5C and 5D: Validation of the astro-silencing construct with a siGFP into BAC-GLT1-eGFP mice.
Figure 5B:
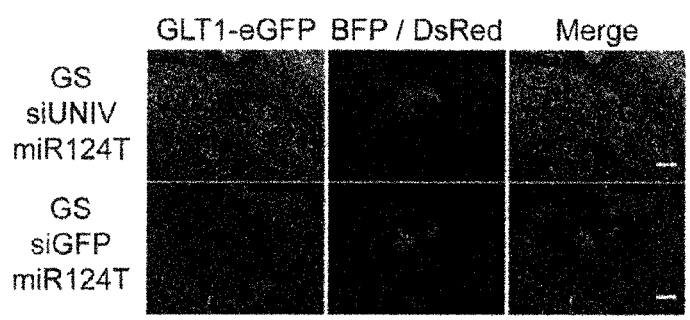
Figure 5C:
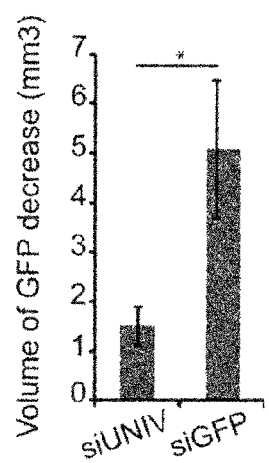
Figure 5D:
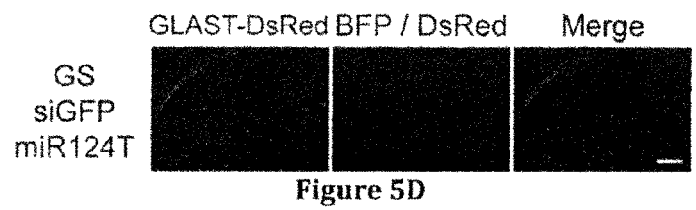

To validate the efficacy of the astro-silencing, the inventors cloned a siRNA directed against the GFP (siGFP). As control, they have used a universal siRNA (siUNIV), a negative control designed to have no homology to known gene sequences. The LVs-W-GS-siGFP/siUNIV were pseudotyped with MOK-G. They have injected them in adult BAC-GLT1-eGFP mice. To visualize the injection site, they have co-injected a LV expressing the BFP or the DsRed, respectively. Two weeks later, mice were sacrificed and direct fluorescence of striatum sections observed (FIG. 5). The inventors can clearly see a decrease of the GFP expression in animals injected with the siGFP in the red area (FIG. 5B-C); whereas, for animals injected with the siUNIV, such a silencing is not observed (FIG. 5B-C). Measure of GFP-less area confirms those observations. The volume of GFP decreases significantly more with the siGFP than with the siUNIV (5.1±1.4 mm$^3$ vs 1.5±0.4 mm$^3$; unpaired t test, P=0.0161) (FIG. 5C).

To exclude a potential non-specific loss of GFP expression due to either the surgical procedure or the injection of viral particles, the inventors have tested this construct in BAC-GLAST-DsRed mice. They have not observed any alteration of DsRed expression (FIG. 5D) confirming the efficacy of the silencing.

Specificity of the Astro-Silencing Construct

Figure 6A:
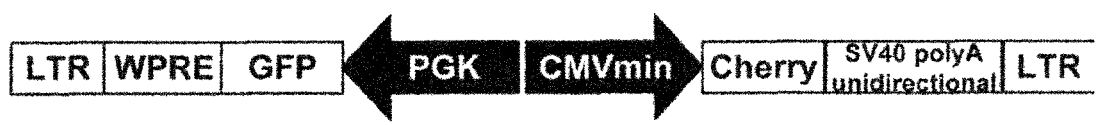
FIGS. 6A and 6B: Specificity of the astro-silencing construct.

To test the selectivity of their astro-silencing construct (i.e. absence or residual silencing in neurons), the inventors have used a vector carrying a bicistronic cassette and expressing both the Cherry and the GFP reporter genes in all infected cells (LV-Cherry-GFP) (FIG. 6A). The LV-Cherry-GFP was pseudotyped with VSV-G to transduce neurons (Naldini et al., 1996). In this context, two scenario could occur: i) a decrease in Cherry/GFP fluorescent ratio reflecting a residual silencing of GFP expression in neurons or ii) no change in Cherry/GFP fluorescent ratio demonstrating the tissue-specificity of the silencing.

Figure 6B:
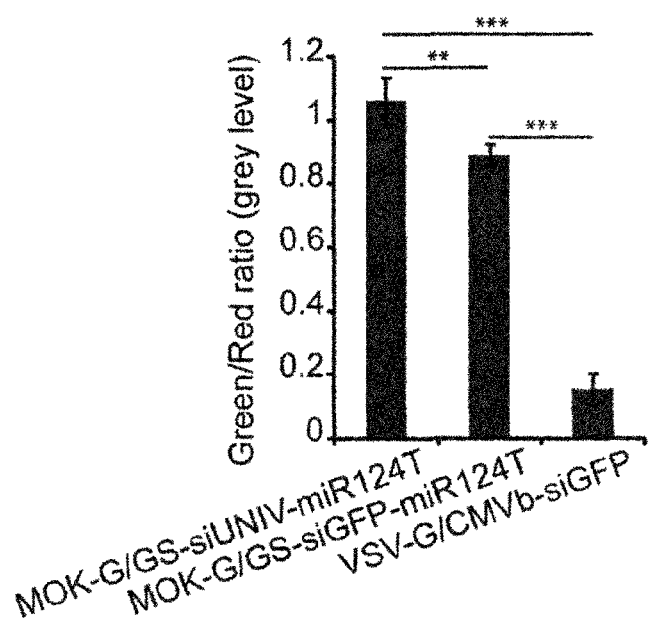

Adult C57/bl6 mice were co-injected with the LV-Cherry-GFP and either the LV-GS-siUNIV or the LV-GS-siGFP. Two weeks later, mice were sacrificed and striatum sections analyzed. The green/red ratio obtained with the control siUNIV (1.06±0.07) represents the reference for the experiment. When the inventors used, as positive control, LV-CMVb-siGFP pseudotyped with VSV-G (neuronal condition), the green/red ratio is drastically decreased (0.15±0.05; $P<0.001$, one-way ANOVA with Newman-Keuls post-hoc test). When LV-Cherry-GFP is co-injected with LV-GS-siGFP, the green/red ratio (0.89±0.03) is slightly decreased by 16% ($P<0.01$, one-way ANOVA with Newman-Keuls post-hoc test) compared to the control LV-GS-siUNIV (FIG. 6). These results are in agreement with residual activity of our astro-silencing construct in neurons (FIG. 4).

Impact of Pseudotyping and Promoters on VSV-G Tropism

The inventors have re-investigated the paradigm of the promoter-dependence tropism of VSV-G pseudotyped LVs. Indeed, some studies have shown that LVs pseudotyped with VSV-G and carrying an astrocytic promoter (such as GFAP or CMV) lead to an astrocytic tropism (Jakobsson et al., 2003; Meunier et al., 2008; Miletic et al., 2004).

Figure 7A:
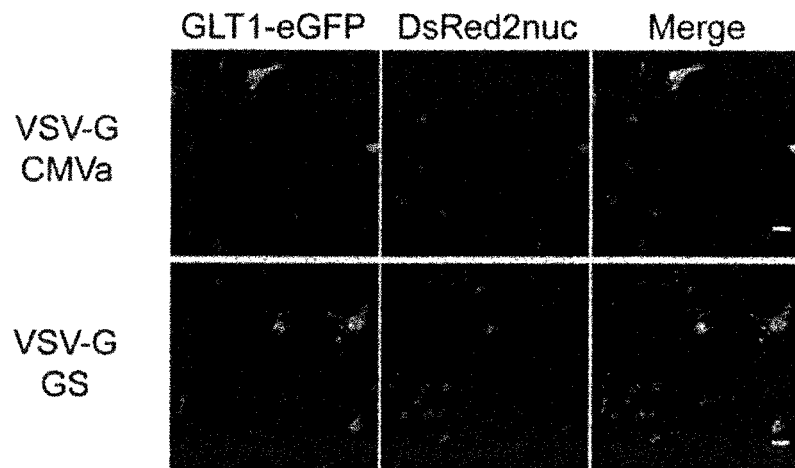
FIGS. 7A and 7B: Tropism of lentiviral vectors with a VSV-G envelope and astrocytic promoters.
Figure 7B:
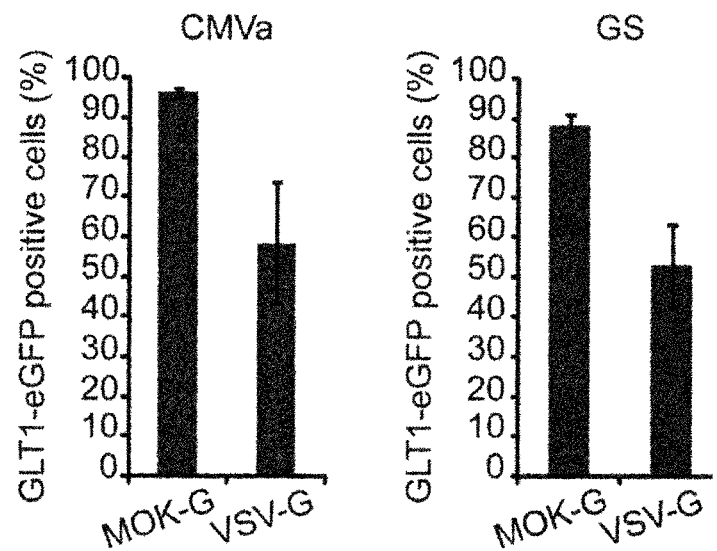
Figure 10A:
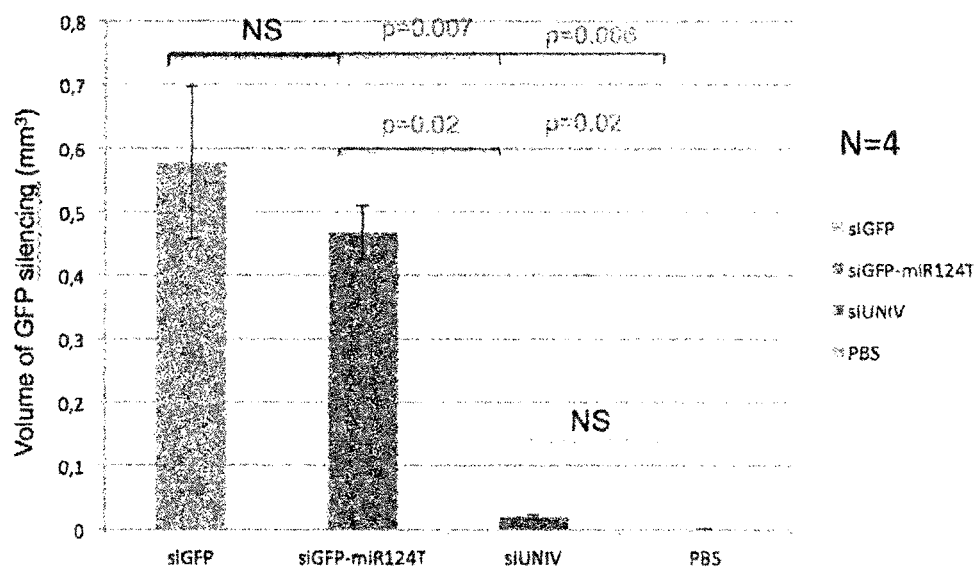
FIGS. 10A and 10B: GFP silencing in neurons when appending miR124T directly to siGFP siRNA.
Figure 10B:
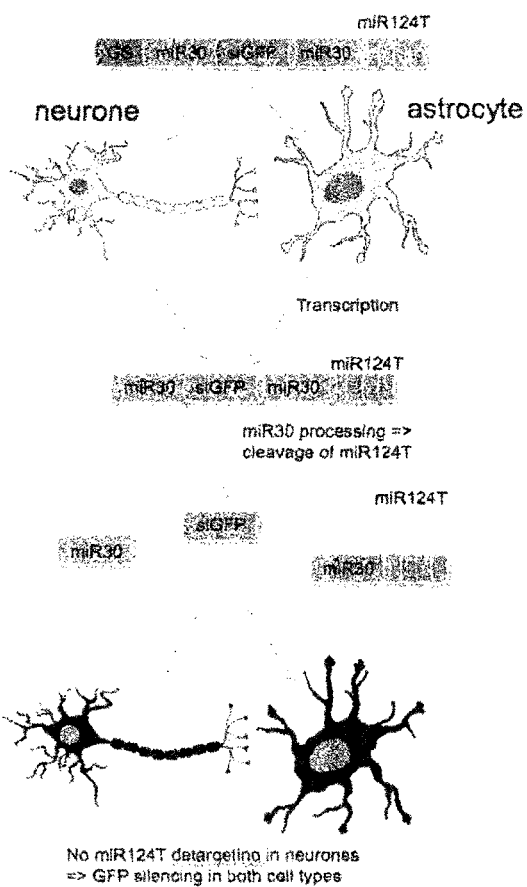

Therefore, they have used PGK, CMVa and GS which were inserted into SIN-W-DsRed2nuc. VSV-G pseudotyped LVs were administered into adult BAC-GLT1-eGFP mice, and three weeks later, mice were sacrificed and striatum sections processed for fluorescence immunostaining. They first assess the tropism by quantify the co-localization between DsRed2nuc and either NeuN or GLT1-eGFP staining (FIG. 7). LV carrying PGK was shown to be highly neurotropic. Interestingly, LVs with either CMVa or GS show a partial astrocytic tropism (58.3±15.2% and 52.8±10.3%, respectively) (FIG. 7). These data confirm the promoter-dependence of VSV-G envelope when compared to results obtained with the MOK-G envelope.

miR124T Detargeting Strategy and VSV-G Tropism

To further improve the astrocytic tropism of VSV-G, the inventors added the miR124T to SIN-W-GS-DsRed2nuc. BAC-GLT1-eGFP mice were injected and sacrificed three weeks later. Co-localization analysis shows that addition of miR124T enhances astrocytic tropism by 1.6-fold (52.8±10.3% without miR124T vs 85±8.2% with miR124T) (FIG. 8). Furthermore, they have compared VSV-G and MOK-G pseudotyped LVs for three main features important for in vivo experiments: i) the transduction volume, ii) the number of transduced cells, and iii) the MFI/cell. No significant differences were measured, although a weak tendency seems to appear in favor of MOK-G concerning the two first points (FIG. 8). Finally, they have evaluated the potential of VSV-G pseudotyped LVs to silence specifically a transgene in astrocytes. LV-GS-siGFP was pseudotyped with VSV-G and co-injected into BAC-GLT1-eGFP mice with a LV expressing the DsRed to localize the injection area. Two weeks later, mice were sacrificed and striatum sections directly observed for endogenous fluorescence. As observed with LV-GS-siGFP pseudotyped with MOK-G, they have obtained a large GFP-less volume (FIG. 9). This consolidates the previous results and substantiates the potency of VSV-G pseudotyped LVs for antro-specific silencing.

Discussion

Tools allowing local and cell-type specific silencing is an essential prerequisite to further reveal cell-autonomous functions and identify processes that depend on cell-cell interactions in neurodegenerative diseases. In the present study the inventors developed a system to selectively silence a ubiquitous gene in astrocytes, based on MOK-G- or VSV-G-LVs carrying an astrocytic promoter, the miR124T sequence and an inducible system.

Previous studies have shown that MOK-G pseudotyped LVs with a CMV promoter have a partial tropism for astrocytes (Cannon et al., 2010; Desmaris et al., 2001; Pertusa et al., 2008; Watson et al., 2002). Although CMV is a ubiquitous promoter, it has been shown to be more astrocytic than neuronal (Jakobsson et al., 2003; Li et al., 2010; Meunier et al., 2008) may be as a consequence of the inhibition of CMV neuronal activity by surrounding astrocytes (Kugler et al., 2001; Sarkis et al., 2000). Hence, a partial astrocytic targeting could be achieved with MOK-G pseudotyped LVs and an ubiquitous promoter.

To improve the tissue-specific expression, the inventors compare MOK-G pseudotyped LVs carrying three astrocytic promoters. The tropism was investigated in transgenic mice expressing the GFP reporter gene under the control of the glutamate transporter 1 (GLT1 aka solute carrier family 1 member 2, Slc1a2) promoter (Regan et al., 2007). GLT1 is the dominant glutamate transporter throughout the forebrain and the spinal cord (Berger and Hediger, 1998; Furuta et al., 1997) and has been considered as an astroglial protein (Chaudhry et al., 1995; Lehre et al., 1995; Rothstein et al., 1994; Torp et al., 1994; Yang et al., 2011). Nonetheless, GLT1 promoter has also low neuronal activity in specific area of the brain (Chen et al., 2002; de Vivo et al., 2010; Mennerick et al., 1998); notably in the neocortex and the hippocampus (de Vivo et al., 2010). However, the neuronal expression of GLT1 is observed during development or after injury (Martin et al., 1997; Mennerick et al., 1998; Northington et al., 1999). When injected in the striatum of adult mice, more than 92% of tranduced cells expressing the DsRednuc reporter gene co-localized with GLT1-GFP. These data demonstrate that EAAT1, GFA-ABC1D and GS promoters improve the tropism of LV, as previously reported for the GFAP promoter (Jakobsson et al., 2003; Kuroda et al., 2008; Liu et al., 2008).

The addition of the miR124T sequence further improves this astrocytic targeting (Colin et al., 2009). The miR124T target sequence acts at the post-transcriptional level, by inducing the degradation of the mRNA (Brown et al., 2007b; Brown et al., 2006). This detargeting effect is particularly evident for GS. Indeed, albeit GS is highly expressed in astrocytes and in liver, the promoter is also active at a lower level in neurons (Mearow et al., 1989; Mill et al., 1991). Thus, addition of miR124T sequence in the LV backbone prevents the neuronal expression of the transgene. The inventors then combined this GS-miR124T with the tetracycline regulated system (Vigna et al., 2005). First of all, they assessed the tropism of this construct with the nuclear-localized GFP and shown that if they target preferentially astrocytes, the residual expression in neurons was higher than with the constitutive system. Similar results were obtained with a siRNA targeting the GFP. One hypothesis to explain this difference is that the tetracycline system is creating amplification loop, which enhances transgene expression (Blench et al., 2005; Regulier et al., 2002). So, it is conceivable in the constitutive system the weak GS transcriptional activity was not associated with detectable transgene expression in neurons whereas in the inducible system, residual reporter gene expression was measured. One possibility to overcome this partial leakiness of the system would be to incorporate not only miR124T sequence but combine several miRT to provide an additive or synergistic effects as previously reported (Brown et al., 2007b; Doench et al., 2003). Indeed, combinatorial arrangement of tissue-specific miRNA-targets efficiently suppresses transgene expression (Brown et al., 2007b). Therefore, the use of several neuronal-specific miRNAs, such as the miR124 and miR10 (Smith et al., 2010) could be considered to prevent more effectively the neuronal transgene expression. As an alternative, one could consider to use an astrocytic minimal promoter instead of the human CMV minimal promoter in the tetracycline system. The use of a glial core promoter, such as the core promoter of the human glutamate carboxypeptidase II or the human JC papovavirus promoter (Han et al., 2007; Krebs et al., 1995), instead of a CMV core promoter should prevent neuronal expression. Finally, a better characterization of astrocytes-specific promoters may further improve tissue-specific expression in the brain (ENCODE and Pleiade projects) (D'Souza et al., 2008; ENCODE, 2004; Portales-Casamar et al., 2010; Yang et al., 2009).

To test the silencing system, the inventors have used a siRNA directed against the GFP reporter gene embedded in a miR30 sequence (Shin et al., 2006). The efficacy of the silencing was demonstrated in BAC-GLT1-eGFP mice. To exclude potential non-specific effects of the LV due to the surgical procedure, injection of viral particles and potential impact on GLT1 promoter activity (Place et al., 2008), they used BAC-GLAST-DsRed mice and they shown that the silencing was specific. Recently, Liu and colleagues have used a miR30-based gene driven by the GFA-ABC1D promoter to express siRNA (Liu et al., 2010). However, in this study, the tropism of the vector was not assessed in vivo. The proof-of-principle study was limited to luciferase measurement in the brain, whether this signal was exclusively due to transgene expression in astrocytes was not investigated. Furthermore, they perform triple injections of LVs which can lead to an astrogliosis, modifying the natural tropism of LVs.

In the last part of study, the inventors have re-investigated the potential of VSV-G pseudotyping LVs for astrocytic targeting. VSV-G envelope is of particular interest because viral vectors are easier to produce and have higher viral titers than with MOK-G envelope (Colin et al., 2009; Desmaris et al., 2001; Liu et al., 2008). Here, they confirmed the promoter-dependence on the tropism of VSV-G pseudotyped LV (Jakobsson et al., 2003; Liu et al., 2010; Meunier et al., 2008; Miletic et al., 2004). The receptor for VSV-G is still unknown: phosphatidylserine has first been proposed (Schlegel et al., 1983), but following studies suggest that it is enhancing viral entry and is not the receptor for the VSV-G envelope (Coil and Miller, 2004, 2005). Recently, it has been shown that the endoplasmic reticulum chaperone gp96, ubiquitously expressed, is essential for the occurrence of functional VSV-G receptors at the cell surface (Bloor et al., 2010). This finding provides evidence for a broad host range of VSV-G pseudotyped LVs including neurons and astrocytes. Hence, tropism of VSV-G pseudotyped LVs is the result of the combined effect of the envelope and the promoter. By combining the VSV-G pseudotyping with GS promoter, miR124T, and an inducible system, the inventors finally show that an astrocytic silencing is efficiently achieved.

These vectors would be particularly suitable for HD study. Indeed, GS promoter activity is not affected by the expression of mHtt. The protein level is unaltered in HD patients (Carter, 1982) and in R6/2 HD transgenic mice (Behrens et al., 2002).

REFERENCES

1. Adra, C. N., Boer, P. H., and McBurney, M. W. (1987). Cloning and expression of the mouse pgk-1 gene and the nucleotide sequence of its promoter. Gene 60, 65-74.
2. Behrens, P. F., Franz, P., Woodman, B., Lindenberg, K. S., and Landwehrmeyer, G. B. (2002). Impaired glutamate transport and glutamate-glutamine cycling: downstream effects of the Huntington mutation. Brain 125, 1908-1922.
3. Berger, U. V., and Hediger, M. A. (1998). Comparative analysis of glutamate transporter expression in rat brain using differential double in situ hybridization. Anat Embryol (Berl) 198, 13-30.
4. Blesch, A., Conner, J., Pfeifer, A., Gasmi, M., Ramirez, A., Britton, W., Alfa, R., Verma, I., and Tuszynski, M. H. (2005). Regulated lentiviral NGF gene transfer controls rescue of medial septal cholinergic neurons. Mol Ther 11, 916-925.
5. Bloor, S., Maelfait, J., Krumbach, R., Beyaert, R., and Randow, F. (2010). Endoplasmic reticulum chaperone gp96 is essential for infection with vesicular stomatitis virus. Proc Natl Acad Sci USA 107, 6970-6975.
6. Boudreau, R. L., Martins, I., and Davidson, B. L. (2009). Artificial microRNAs as siRNA shuttles: improved safety as compared to shRNAs in vitro and in vivo. Mol Ther 17, 169-175.
7. Boudreau, R. L., Monteys, A. M., and Davidson, B. L. (2008). Minimizing variables among hairpin-based RNAi vectors reveals the potency of shRNAs. RNA 14, 1834-1844.
8. Brown, B. D., Cantore, A., Annoni, A., Sergi, L. S., Lombardo, A., Della Valle, P., D'Angelo, A., and Naldini, L. (2007a). A microRNA-regulated lentiviral vector mediates stable correction of hemophilia B mice. Blood 110, 4144-4152.
9. Brown, B. D., Gentner, B., Cantore, A., Colleoni, S., Amendola, M., Zingale, A., Baccarini, A., Lazzari, G., Galli, C., and Naldini, L. (2007b). Endogenous microRNA can be broadly exploited to regulate transgene expression according to tissue, lineage and differentiation state. Nat Biotechnol 25, 1457-1467.
10. Brown, B. D., Venneri, M. A., Zingale, A., Sergi Sergi, L., and Naldini, L. (2006). Endogenous microRNA regulation suppresses transgene expression in hematopoietic lineages and enables stable gene transfer. Nat Med 12, 585-591.
11. Cannon, J. R., Sew, T., Montero, L., Burton, E. A., and Greenamyre, J. T. (2010). Pseudotype-dependent lentiviral transduction of astrocytes or neurons in the rat substantia nigra. Exp Neurol. 228, 41-52
12. Carter, C. J. (1982). Glutamine synthetase activity in Huntington's disease. Life Sci 31, 1151-1159.
13. Chaudhry, F. A., Lehre, K. P., van Lookeren Campagne, M., Ottersen, O. P., Danbolt, N. C., and Storm-Mathisen, J. (1995). Glutamate transporters in glial plasma membranes: highly differentiated localizations revealed by quantitative ultrastructural immunocytochemistry. Neuron 15, 711-720.

14. Chen, W., Aoki, C., Mahadomrongkul, V., Gruber, C. E., Wang, G. J., Blitzblau, R., Irwin, N., and Rosenberg, P. A. (2002). Expression of a variant form of the glutamate transporter GLT1 in neuronal cultures and in neurons and astrocytes in the rat brain. J Neurosci 22, 2142-2152.

15. Coil, D. A., and Miller, A. D. (2004). Phosphatidylserine is not the cell surface receptor for vesicular stomatitis virus. J Virol 78, 10920-10926.

16. Coil, D. A., and Miller, A. D. (2005). Enhancement of enveloped virus entry by phosphatidylserine. J Virol 79, 11496-11500.

17. Colin, A., Faideau, M., Dufour, N., Auregan, G., Hassig, R., Andrieu, T., Brouillet, E., Hantraye, P., Bonvento, G., and Deglon, N. (2009). Engineered lentiviral vector targeting astrocytes in vivo. Glia 57, 667-679.

18. D'Souza, C. A., Chopra, V., Varhol, R., Xie, Y. Y., Bohacec, S., Zhao, Y., Lee, L. L., Bilenky, M., Portales-Casamar, E., He, A., et al. (2008). Identification of a set of genes showing regionally enriched expression in the mouse brain. BMC Neurosci 9, 66.

19. de Vivo, L., Melone, M., Rothstein, J. D., and Conti, F. (2010). GLT-1 Promoter Activity in Astrocytes and Neurons of Mouse Hippocampus and Somatic Sensory Cortex. Front Neuroanat 3, 31.

20. Deglon, N., Tseng, J. L., Bensadoun, J. C., Zurn, A. D., Arsenijevic, Y., Pereira de Almeida, L., Zufferey, R., Trono, D., and Aebischer, P. (2000). Self-inactivating lentiviral vectors with enhanced transgene expression as potential gene transfer system in Parkinson's disease. Hum Gene Ther 11, 179-190.

21. Deo, M., Yu, J. Y., Chung, K. H., Tippens, M., and Turner, D. L. (2006). Detection of mammalian microRNA expression by in situ hybridization with RNA oligonucleotides. Dev Dyn 235, 2538-2548.

22. Desmaris, N., Bosch, A., Salaun, C., Petit, C., Prevost, M. C., Tordo, N., Perrin, P., Schwartz, O., de Rocquigny, H., and Heard, J. M. (2001). Production and neurotropism of lentivirus vectors pseudotyped with lyssavirus envelope glycoproteins. Mol Ther 4, 149-156.

23. Doench, J. G., Petersen, C. P., and Sharp, P. A. (2003). siRNAs can function as miRNAs. Genes Dev 17, 438-442.

24. ENCODE (2004). The ENCODE (ENCyclopedia Of DNA Elements) Project. Science 306, 636-640.

25. Franklin, K., and Paxinos, G. (1997). The Mouse Brain in Stereotaxic Coordinates. San Diego: Academic Press.

26. Furuta, A., Rothstein, J. D., and Martin, L. J. (1997). Glutamate transporter protein subtypes are expressed differentially during rat CNS development. J Neurosci 17, 8363-8375.

27. Han, L., Wong, D. L., Tsai, G., Jiang, Z., and Coyle, J. T. (2007). Promoter analysis of human glutamate carboxypeptidase II. Brain Res 1170, 1-12.

28. Hottinger, A. F., Azzouz, M., Deglon, N., Aebischer, P., and Zurn, A. D. (2000). Complete and long-term rescue of lesioned adult motoneurons by lentiviral-mediated expression of glial cell line-derived neurotrophic factor in the facial nucleus. J Neurosci 20, 5587-5593.

29. Jakobsson, J., Ericson, C., Jansson, M., Bjork, E., and Lundberg, C. (2003). Targeted transgene expression in rat brain using lentiviral vectors. J Neurosci Res 73, 876-885.

30. Jakobsson, J., and Lundberg, C. (2006). Lentiviral vectors for use in the central nervous system. Mol Ther 13, 484-493.

31. Kim, S. Y., Choi, S. Y., Chao, W., and Volsky, D. J. (2003). Transcriptional regulation of human excitatory amino acid transporter 1 (EAAT1): cloning of the EAAT1 promoter and characterization of its basal and inducible activity in human astrocytes. J Neurochem 87, 1485-1498.

32. Krebs, C. J., McAvoy, M. T., and Kumar, G. (1995). The JC virus minimal core promoter is glial cell specific in vivo. J Virol 69, 2434-2442.

33. Kugler, S., Meyn, L., Holzmuller, H., Gerhardt, E., Isenmann, S., Schulz, J. B., and Bahr, M. (2001). Neuron-specific expression of therapeutic proteins: evaluation of different cellular promoters in recombinant adenoviral vectors. Mol Cell Neurosci 17, 78-96.

34. Kuroda, H., Kutner, R. H., Bazan, N. G., and Reiser, J. (2008). A comparative analysis of constitutive and cell-specific promoters in the adult mouse hippocampus using lentivirus vector-mediated gene transfer. J Gene Med 10, 1163-1175.

35. Lagos-Quintana, M., Rauhut, R., Yalcin, A., Meyer, J., Lendeckel, W., and Tuschl, T. (2002). Identification of tissue-specific microRNAs from mouse. Curr Biol 12, 735-739.

36. Lee, Y., Messing, A., Su, M., and Brenner, M. (2008). GFAP promoter elements required for region-specific and astrocyte-specific expression. Glia 56, 481-493.

37. Lehre, K. P., Levy, L. M., Ottersen, O. P., Storm-Mathisen, J., and Danbolt, N. C. (1995). Differential expression of two glial glutamate transporters in the rat brain: quantitative and immunocytochemical observations. J Neurosci 15, 1835-1853.

38. Li, M., Husic, N., Lin, Y., Christensen, H., Malik, I., McIver, S., Daniels, C. M., Harris, D. A., Kotzbauer, P. T., Goldberg, M. P., et al. (2010). Optimal promoter usage for lentiviral vector-mediated transduction of cultured central nervous system cells. J Neurosci Methods 189, 56-64.

39. Liu, B., Paton, J. F., and Kasparov, S. (2008). Viral vectors based on bidirectional cell-specific mammalian promoters and transcriptional amplification strategy for use in vitro and in vivo. BMC Biotechnol 8, 49.

40. Liu, B., Xu, H., Paton, J. F., and Kasparov, S. (2010). Cell- and region-specific miR30-based gene knock-down with temporal control in the rat brain. BMC Mol Biol 11, 93.

41. Martin, L. J., Brambrink, A. M., Lehmann, C., Portera-Cailliau, C., Koehler, R., Rothstein, J., and Traystman, R. J. (1997). Hypoxia-ischemia causes abnormalities in glutamate transporters and death of astroglia and neurons in newborn striatum. Ann Neurol 42, 335-348.

42. McBride, J. L., Boudreau, R. L., Harper, S. Q., Staber, P. D., Monteys, A. M., Martins, I., Gilmore, B. L., Burstein, H., Peluso, R. W., Polisky, B., et al. (2008). Artificial miRNAs mitigate shRNA-mediated toxicity in the brain: implications for the therapeutic development of RNAi. Proc Natl Acad Sci USA 105, 5868-5873.

43. Mearow, K. M., Mill, J. F., and Vitkovic, L. (1989). The ontogeny and localization of glutamine synthetase gene expression in rat brain. Brain Res Mol Brain Res 6, 223-232.

44. Mennerick, S., Dhond, R. P., Benz, A., Xu, W., Rothstein, J. D., Danbolt, N. C., Isenberg, K. E., and Zorumski, C. F. (1998). Neuronal expression of the glutamate transporter GLT-1 in hippocampal microcultures. J Neurosci 18, 4490-4499.

45. Meunier, A., Mauborgne, A., Masson, J., Mallet, J., and Pohl, M. (2008). Lentiviral-mediated targeted transgene expression in dorsal spinal cord glia: tool for the study of 46. Miletic, H., Fischer, Y. H., Neumann, H., Hans, V., Stenzel, W., Giroglou, T., Hermann, M., Deckert, M., and Von Laer, D. (2004). Selective transduction of malignant glioma by lentiviral vectors pseudotyped with lymphocytic choriomeningitis virus glycoproteins. Hum Gene Ther 15, 1091-1100.
47. Mill, J. F., Mearow, K. M., Purohit, H. J., Haleem-Smith, H., King, R., and Freese, E. (1991). Cloning and functional characterization of the rat glutamine synthetase gene. Brain Res Mol Brain Res 9, 197-207.
48. Mishima, T., Mizuguchi, Y., Kawahigashi, Y., and Takizawa, T. (2007). RT-PCR-based analysis of microRNA (miR-1 and -124) expression in mouse CNS. Brain Res 1131, 37-43.
49. Naldini, L., Blomer, U., Gallay, P., Ory, D., Mulligan, R., Gage, F. H., Verma, I. M., and Trono, D. (1996). In vivo gene delivery and stable transduction of nondividing cells by a lentiviral vector. Science 272, 263-267.
50. Northington, F. J., Traystman, R. J., Koehler, R. C., and Martin, L. J. (1999). GLT1, glial glutamate transporter, is transiently expressed in neurons and develops astrocyte specificity only after midgestation in the ovine fetal brain. J Neurobiol 39, 515-526.
51. Pertusa, M., Garcia-Matas, S., Mammeri, H., Adell, A., Rodrigo, T., Mallet, J., Cristofol, R., Sarkis, C., and Sanfeliu, C. (2008). Expression of GDNF transgene in astrocytes improves cognitive deficits in aged rats. Neurobiol Aging 29, 1366-1379.
52. Place, R. F., Li, L. C., Pookot, D., Noonan, E. J., and Dahiya, R. (2008). MicroRNA-373 induces expression of genes with complementary promoter sequences. Proc Natl Acad Sci USA 105, 1608-1613.
53. Portales-Casamar, E., Swanson, D. J., Liu, L., de Leeuw, C. N., Banks, K. G., Ho Sui, S. J., Fulton, D. L., Ali, J., Amirabbasi, M., Arenillas, D. J., et al. (2010). A regulatory toolbox of MiniPromoters to drive selective expression in the brain. Proc Natl Acad Sci USA 107, 16589-16594.
54. Regan, M. R., Huang, Y. H., Kim, Y. S., Dykes-Hoberg, M. I., Jin, L., Watkins, A. M., Bergles, D. E., and Rothstein, J. D. (2007). Variations in promoter activity reveal a differential expression and physiology of glutamate transporters by glia in the developing and mature CNS. J Neurosci 27, 6607-6619.
55. Regulier, E., Pereira de Almeida, L., Sommer, B., Aebischer, P., and Deglon, N. (2002). Dose-dependent neuroprotective effect of ciliary neurotrophic factor delivered via tetracycline-regulated lentiviral vectors in the quinolinic acid rat model of Huntington's disease. Hum Gene Ther 13, 1981-1990.
56. Rothstein, J. D., Martin, L., Levey, A. I., Dykes-Hoberg, M., Jin, L., Wu, D., Nash, N., and Kuncl, R. W. (1994). Localization of neuronal and glial glutamate transporters. Neuron 13, 713-725.
57. Sarkis, C., Serguera, C., Petres, S., Buchet, D., Ridet, J. L., Edelman, L., and Mallet, J. (2000). Efficient transduction of neural cells in vitro and in vivo by a baculovirus-derived vector. Proc Natl Acad Sci USA 97, 14638-14643.
58. Schlegel, R., Tralka, T. S., Willingham, M. C., and Pastan, I. (1983). Inhibition of VSV binding and infectivity by phosphatidylserine: is phosphatidylserine a VSV-binding site? Cell 32, 639-646.
59. Shin, K. J., Wall, E. A., Zavzavadjian, J. R., Santat, L. A., Liu, J., Hwang, J. I., Rebres, R., Roach, T., Seaman, W., Simon, M. I., et al. (2006). A single lentiviral vector platform for microRNA-based conditional RNA interference and coordinated transgene expression. Proc Natl Acad Sci USA 103, 13759-13764.
60. Slezak, M., Goritz, C., Niemiec, A., Frisen, J., Chambon, P., Metzger, D., and Pfrieger, F. W. (2007). Transgenic mice for conditional gene manipulation in astroglial cells. Glia 55, 1565-1576.
61. Smirnova, L., Grafe, A., Seiler, A., Schumacher, S., Nitsch, R., and Wulczyn, F. G. (2005). Regulation of miRNA expression during neural cell specification. Eur J Neurosci 21, 1469-1477.
62. Smith, B., Treadwell, J., Zhang, D., Ly, D., McKinnell, I., Walker, P. R., and Sikorska, M. (2010). Large-scale expression analysis reveals distinct microRNA profiles at different stages of human neurodevelopment. PLoS One 5, e11109.
63. Torp, R., Danbolt, N. C., Babaie, E., Bjoras, M., Seeberg, E., Storm-Mathisen, J., and Ottersen, O. P. (1994). Differential expression of two glial glutamate transporters in the rat brain: an in situ hybridization study. Eur J Neurosci 6, 936-942.
64. Vigna, E., Amendola, M., Benedicenti, F., Simmons, A. D., Follenzi, A., and Naldini, L. (2005). Efficient Tet-dependent expression of human factor IX in vivo by a new self-regulating lentiviral vector. Mol Ther 11, 763-775.
65. Watson, D. J., Kobinger, G. P., Passini, M. A., Wilson, J. M., and Wolfe, J. H. (2002). Targeted transduction patterns in the mouse brain by lentivirus vectors pseudotyped with VSV, Ebola, Mokola, LCMV, or MuLV envelope proteins. Mol Ther 5, 528-537.
66. Wong, L. F., Goodhead, L., Prat, C., Mitrophanous, K. A., Kingsman, S. M., and Mazarakis, N. D. (2006). Lentivirus-mediated gene transfer to the central nervous system: therapeutic and research applications. Hum Gene Ther 17, 1-9.
67. Yang, G. S., Banks, K. G., Bonaguro, R. J., Wilson, G., Dreolini, L., de Leeuw, C. N., Liu, L., Swanson, D. J., Goldowitz, D., Holt, R. A., et al. (2009). Next generation tools for high-throughput promoter and expression analysis employing single-copy knock-ins at the Hprt1 locus. Genomics 93, 196-204.
68. Yang, Y., Vidensky, S., Jin, L., Jie, C., Lorenzini, I., Frankl, M., and Rothstein, J. D. (2011). Molecular comparison of GLT1+ and ALDH1L1+ astrocytes in vivo in astroglial reporter mice. Glia 59, 200-207.

The invention claimed is:

1. A viral vector for silencing a gene specifically in astrocytes comprising:

an astrocyte-specific viral envelope protein, a first nucleic acid sequence encoding a transcription activator and at least one target sequence of a neuron-specific microRNA (miR) under the control of an astrocyte-specific promoter, and a second nucleic acid sequence encoding a RNA for silencing the gene under the control of a promoter inducible by the transcription activator, wherein the first and second nucleic acid sequences are on the same nucleic acid molecule.

2. The viral vector according to claim 1, wherein the astrocyte-specific viral envelope protein is Mokola virus G protein (G-MOK).

3. The viral vector according to claim 1, wherein the transcription activator is the tetracycline transactivator (tTA) and the promoter inducible by the transcription activator is the tetracycline response element (TRE).

4. The viral vector according to claim 3, wherein the astrocyte specific promoter is the promoter of rat GS gene.

5. The viral vector according to claim 1, wherein the astrocyte specific promoter is the promoter of the glutamine synthase (GS) gene.

6. The viral vector according to claim 1, wherein the target sequence of the neuron-specific miR is a target sequence of miR124 (miR124T).

7. The viral vector according to claim 1, wherein the nucleic acid sequence encoding a RNA for silencing the gene encodes a siRNA or a shRNA targeting the gene mRNA.

8. The viral vector according to claim 7, wherein the shRNA is embedded in a miR sequence.

9. The viral vector according to claim 8, wherein the miR sequence is a miR30 sequence.

10. The viral vector according to claim 1, wherein the viral vector is a lentiviral vector.

11. The viral vector according to claim 10, wherein the lentiviral vector is an HIV-1 vector.

12. The viral vector according to claim 9, wherein the nucleic acid molecule comprises, from 5' to 3':

a 5' long terminal repeat (LTR) sequence, a sequence encoding a shRNA targeting the gene embedded in a miR30 sequence, the GS rat promoter,
a sequence encoding the tetracycline transactivator
the woodchuck hepatitis post-transcriptional regulatory element (WPRE)
a sequence encoding 4 copies of a miR124 target sequence,
a 3' long terminal repeat (LTR) sequence comprising the tetracycline response element (TRE).

13. The viral vector according to claim 1, wherein the gene is the huntingtin gene.

14. The viral vector according to claim 1, for use in the prevention or treatment of astrocyte-mediated diseases.

15. A pharmaceutical composition comprising a viral vector according to claim 1 as an active ingredient and a pharmaceutically acceptable vehicle or excipient.

16. An in vitro method, of silencing a gene in astrocytes, comprising contacting the viral vector according to claim 1 with at least one astrocyte.

17. A nucleic acid molecule comprising from 5' to 3':
a 5' long terminal repeat (LTR) sequence,
a sequence comprising from 4 to 1000 nucleotides,
the GS rat promoter,
a sequence encoding the tetracycline transactivator,
the woodchuck hepatitis post-transcriptional regulatory element (WPRE),
a sequence encoding 4 copies of a miR124 target sequence,
a 3' long terminal repeat (LTR) sequence comprising the tetracycline response element (TRE).

18. The nucleic acid sequence according to claim 17, wherein the sequence comprising from 4 to 1000 nucleotides is a multiple cloning site.

19. The nucleic acid sequence according to claim 17, wherein the sequence comprising from 4 to 1000 nucleotides is sequence encoding a siRNA or a shRNA.

* * * * *

SEQUENCE LISTING

<160> NUMBER OF SEQ ID NOS: 19

<210> SEQ ID NO 1
<211> LENGTH: 747
<212> TYPE: DNA
<213> ORGANISM: Artificial
<220> FEATURE:

<223> OTHER INFORMATION: Tetracycline trasactivator coding sequence

<400> SEQUENCE: 1

```
atgtctagac tggacaagag caaagtcata aactctgctc tggaattact caatgaagtc      60
ggtatcgaag gcctgacgac aaggaaactc gctcaaaagc tgggagttga gcagcctacc     120
ctgtactggc acgtgaagaa caagcgggcc ctgctcgatg ccctggcaat cgagatgctg     180
gacaggcatc ataccccactt ctgccccctg gaaggcgagt catggcaaga ctttctgcgg     240
aacaacgcca gtcattccg ctgtgctctc ctctcacatc gcgacggggc taaagtgcat      300
ctcggcaccc gcccaacaga gaaacagtac gaaaccctgg aaaatcagct cgcgttcctg     360
tgtcagcaag gcttctccct ggagaacgca ctgtacgctc tgtccgccgt gggccacttt     420
acactgggct gcgtattgga ggatcaggag catcaagtag caaaagagga aagagagaca     480
cctaccaccg attctatgcc cccacttctg agacaagcaa ttgagctgtt cgaccatcag     540
ggagccgaac ctgccttcct tttcggcctg gaactaatca tatgtggcct ggagaaacag     600
ctaaagtgcg aaagcggcgg gccggccgac gcccttgacg attttgactt agacatgctc     660
ccagccgatg cccttgacga cttttgacctt gatatgctgc ctgctgacgc tcttgacgat     720
tttgaccttg acatgctccc cgggtaa                                         747
```

<210> SEQ ID NO 2
<211> LENGTH: 277
<212> TYPE: DNA
<213> ORGANISM: Artificial
<220> FEATURE:
<223> OTHER INFORMATION: Tetracycline response element

<400> SEQUENCE: 2

```
tcgagtttac tccctatcag tgatagagaa cgtatgtcga gtttactccc tatcagtgat      60
agagaacgat gtcgagttta ctccctatca gtgatagaga acgtatgtcg agtttactcc     120
ctatcagtga tagagaacgt atgtcgagtt tactccctat cagtgataga gaacgtatgt     180
cgagtttatc cctatcagtg atagagaacg tatgtcgagt ttactcccta tcagtgatag     240
agaacgtatg tcgaggtagg cgtgtacggt gggaggc                              277
```

<210> SEQ ID NO 3
<211> LENGTH: 433
<212> TYPE: DNA
<213> ORGANISM: Artificial
<220> FEATURE:
<223> OTHER INFORMATION: Rat glutamine synthase promoter

<400> SEQUENCE: 3

```
tggctcgctc aacaaagggt aaaattctct tctggggttc tggatttttca ccgacagatc      60
tctccgaaaa cctctgtact gttaaggtag caaaggacca aggccaaatg acgctgagat     120
agtctcagcc tgggtccgag ggtccagagg tcgctaaaga acgcgtgctg caaaggcgca     180
cagcaccttc ggccccggcc ccccagccgc cgctgcctcc cctccccat tccccttttct     240
cttttctttct tctgggtcgc tcgccccacc ccgcggttcc tcacggctcc tgggccaatg     300
gtctcagggc cccggtgcac agcaactgat gggcacgggg ttccaggcct aggccagcca     360
atcagggcgc ctgggggcgg gcacaagctg ccaataaaaa gtactgagca gcccgcaacc     420
ctccacagcc gag                                                       433
```

<210> SEQ ID NO 4
<211> LENGTH: 21

```
<212> TYPE: DNA
<213> ORGANISM: Artificial
<220> FEATURE:
<223> OTHER INFORMATION: miR124 target coding sequence

<400> SEQUENCE: 4
tggcattcac cgcgtgcctt a                                          21

<210> SEQ ID NO 5
<211> LENGTH: 860
<212> TYPE: DNA
<213> ORGANISM: Artificial sequence
<220> FEATURE:
<223> OTHER INFORMATION: Chimeric 5' LTR sequence

<400> SEQUENCE: 5
aagcttggcc attgcatacg ttgtatccat atcataatat gtacatttat attggctcat    60
gtccaacatt accgccatgt tgacattgat tattgactag ttattaatag taatcaatta   120
cggggtcatt agttcatagc ccatatatgg agttccgcgt tacataactt acggtaaatg   180
gcccgcctgg ctgaccgccc aacgaccccc gcccattgac gtcaataatg acgtatgttc   240
ccatagtaac gccaataggg actttccatt gacgtcaatg ggtggagtat ttacggtaaa   300
ctgcccactt ggcagtacat caagtgtatc atatgccaag tacgccccct attgacgtca   360
atgacggtaa atggcccgcc tggcattatg cccagtacat gaccttatgg gactttccta   420
cttggcagta catctacgta ttagtcatcg ctattaccat ggtgatgcgg ttttggcagt   480
acatcaatgg gcgtggatag cggtttgact cacggggatt tccaagtctc cacccattg   540 acgtcaatgg gagtttgttt tggcaccaaa atcaacggga ctttccaaaa tgtcgtaaca   600
actccgcccc attgacgcaa atgggcggta ggcgtgtacg gtgggaggtc tatataagca   660
gagctcgttt agtgaaccgg ggtctctctg gttagaccag atctgagcct gggagctctc   720
tggctaacta gggaacccac tgcttaagcc tcaataaagc ttgccttgag tgcttcaagt   780
agtgtgtgcc cgtctgttgt gtgactctgg taactagaga tccctcagac ccttttagtc   840
agtgtggaaa atctctagca                                              860

<210> SEQ ID NO 6
<211> LENGTH: 610
<212> TYPE: DNA
<213> ORGANISM: Artificial
<220> FEATURE:
<223> OTHER INFORMATION: Woodchuck hepatitis post-transcriptional
      regulatory element

<400> SEQUENCE: 6
gaattccgat aatcaacctc tggattacaa aatttgtgaa agattgactg gtattcttaa    60
ctatgttgct ccttttacgc tatgtggata cgctgcttta atgcctttgt atcatgctat   120
tgcttcccgt atggctttca ttttctcctc cttgtataaa tcctggttgc tgtctcttta   180
tgaggagttg tgcccgttg tcaggcaacg tggcgtggtg tgcactgtgt ttgctgacgc   240 aaccccact ggttggggca ttgccaccac ctgtcagctc ctttccggga ctttcgcttt   300
ccccctccct attgccacgg cggaactcat cgccgcctgc cttgcccgct gctggacagg   360
ggctcggctg ttgggcactg acaattccgt ggtgttgtcg gggaagctga cgtcctttcc   420
atggctgctc gcctgtgttg ccacctggat tctgcgcggg acgtccttct gctacgtccc   480
ttcggccctc aatccagcgg accttccttc ccgcggcctg ctgccggctc tgcggcctct   540
tccgcgtctt cgccttcgcc ctcagacgag tcggatctcc ctttgggccg cctccccgca   600
```

```
tcgggaattc                                                            610

<210> SEQ ID NO 7
<211> LENGTH: 105
<212> TYPE: DNA
<213> ORGANISM: Artificial
<220> FEATURE:
<223> OTHER INFORMATION: Sequence encoding 4 copies of miR124T

<400> SEQUENCE: 7
tggcattcac cgcgtgcctt aattcgaatg gcattcaccg cgtgccttaa acgcgttggc     60
attcaccgcg tgccttaaat gcattggcat tcaccgcgtg cctta                   105

<210> SEQ ID NO 8
<211> LENGTH: 594
<212> TYPE: DNA
<213> ORGANISM: Artificial
<220> FEATURE:
<223> OTHER INFORMATION: Self-inactivating 3'LTR comprising the CMV
      promoter

<400> SEQUENCE: 8
tggaagggct aattcactcc caacgaagac aagatatgat cccgggctcg agtttaccac     60
tccctatcag tgatagagaa aagtgaaagt cgagtttacc actccctatc agtgatagag    120
aaaagtgaaa gtcgagtttta ccactcccta tcagtgatag agaaaagtga agtcgagtt    180 taccactccc tatcagtgat agagaaaagt gaaagtcgag tttaccactc cctatcagtg    240
atagagaaaa gtgaaagtcg agtttaccac tccctatcag tgatagagaa aagtgaaagt    300
cgagtttacc actccctatc agtgatagag aaaagtgaaa gtcgagctcg gtacccgggt    360
cgagtaggcg ttgatcagat gctgcatata agcagctgct ttttgcttgt actgggtctc    420
tctggttaga ccagatctga gcctgggagc tctctggcta actagggaac ccactgctta    480
agcctcaata aagcttgcct tgagtgcttc aagtagtgtg tgcccgtctg ttgtgtgact    540
ctggtaacta gagatccctc agaccctttt agtcagtgtg gaaaatctct agca         594

<210> SEQ ID NO 9
<211> LENGTH: 64
<212> TYPE: DNA
<213> ORGANISM: Artificial
<220> FEATURE:
<223> OTHER INFORMATION: Anti-huntingtin shRNA coding sequence

<400> SEQUENCE: 9
agcgaagctt tgatggattc taattagtga agccacagat gtaattagaa tccatcaaag     60
ctct                                                                  64

<210> SEQ ID NO 10
<211> LENGTH: 340
<212> TYPE: DNA
<213> ORGANISM: Artificial
<220> FEATURE:
<223> OTHER INFORMATION: miR30-embedded anti-huntingtin shRNA coding
      sequence

<400> SEQUENCE: 10
ggatccgtcg actagggata acagggtaat tgtttgaatg aggcttcagt actttacaga     60
atcgttgcct gcacatcttg gaaacacttg ctgggattac ttcttcaggt taacccaaca    120
gaaggctcga gaaggtatat tgctgttgac agtgagcgaa gctttgatgg attctaatta    180
```

| | |
|---|---|
| gtgaagccac agatgtaatt agaatccatc aaagctctgc ctactgcctc ggaattcaag | 240 |
| gggctacttt aggagcaatt atcttgttta ctaaaactga ataccttgct atctctttga | 300 |
| tacatttta caaagctgaa ttaaaatggt ataaattaaa | 340 |

<210> SEQ ID NO 11
<211> LENGTH: 5457
<212> TYPE: DNA
<213> ORGANISM: Artificial
<220> FEATURE:
<223> OTHER INFORMATION: Construct for inactivating the huntigtin gene specifically in astrocytes

<400> SEQUENCE: 11

| | |
|---|---|
| aagcttggcc attgcatacg ttgtatccat atcataatat gtacatttat attggctcat | 60 |
| gtccaacatt accgccatgt tgacattgat tattgactag ttattaatag taatcaatta | 120 |
| cggggtcatt agttcatagc ccatatatgg agttccgcgt tacataactt acggtaaatg | 180 |
| gcccgcctgg ctgaccgccc aacgaccccc gcccattgac gtcaataatg acgtatgttc | 240 |
| ccatagtaac gccaataggg actttccatt gacgtcaatg ggtggagtat ttacggtaaa | 300 |
| ctgcccactt ggcagtacat caagtgtatc atatgccaag tacgccccct attgacgtca | 360 |
| atgacggtaa atggcccgcc tggcattatg cccagtacat gaccttatgg actttcctta | 420 |
| cttggcagta catctacgta ttagtcatcg ctattaccat ggtgatgcgg ttttggcagt | 480 |
| acatcaatgg gcgtggatag cggtttgact cacggggatt tccaagtctc cacccccattg | 540 |
| acgtcaatgg gagtttgttt tggcaccaaa atcaacggga ctttccaaaa tgtcgtaaca | 600 |
| actccgcccc attgacgcaa atgggcggta ggcgtgtacg gtgggaggtc tatataagca | 660 |
| gagctcgttt agtgaaccgg ggtctctctg gttagaccag atctgagcct gggagctctc | 720 |
| tggctaacta gggaacccac tgcttaagcc tcaataaagc ttgccttgag tgcttcaagt | 780 |
| agtgtgtgcc cgtctgttgt gtgactctgg taactagaga tccctcagac ccttttagtc | 840 |
| agtgtggaaa atctctagca gtggcgcccg aacagggacc tgaaagcgaa agggaaacca | 900 |
| gagctctctc gacgcaggac tcggcttgct gaagcgcgca cggcaagagg cgaggggcgg | 960 |
| cgactggtga gtacgccaaa aattttgact agcggaggct agaaggagag agatgggtgc | 1020 |
| gagagcgtca gtattaagcg ggggagaatt agatcgcgat gggaaaaaat tcggttaagg | 1080 |
| ccaggggga agaaaaaata taattaaaa catatagtat gggcaagcag ggagctagaa | 1140 |
| cgattcgcag ttaatcctgg cctgttagaa acatcagaag gctgtagaca atactggga | 1200 |
| cagctacaac catcccttca gacaggatca gaagaactta gatcattata taatacagta | 1260 |
| gcaaccctct attgtgtgca tcaaaggata gagataaaag acaccaagga agctttagac | 1320 |
| aagatagagg aagagcaaaa caaaagtaag accaccgcac agcaagcggc cgctgatctt | 1380 |
| cagacctgga ggaggagata tgagggacaa ttggagaagt gaattatata aatataaagt | 1440 |
| agtaaaaatt gaaccattag gagtagcacc caccaaggca aagagaagag tggtgcagag | 1500 |
| agaaaaaaga gcagtgggaa taggagcttt gttccttggg ttcttgggag cagcaggaag | 1560 |
| cactatgggc gcagcctcaa tgacgctgac ggtacaggcc agacaattat tgtctggtat | 1620 |
| agtgcagcag cagaacaatt tgctgagggc tattgaggcg caacagcatc tgttgcaact | 1680 |
| cacagtctgg ggcatcaagc agctccaggc aagaatcctg gctgtggaaa gatacctaaa | 1740 |
| ggatcaacag ctcctgggga tttggggttg ctctggaaaa ctcatttgca ccactgctgt | 1800 |
| gccttggaat gctagttgga gtaataaatc tctggaacag atttggaatc acacgacctg | 1860 |

```
gatggagtgg gacagagaaa ttaacaatta cacaagctta atacactcct taattgaaga    1920
atcgcaaaac cagcaagaaa agaatgaaca agaattattg gaattagata aatgggcaag    1980
tttgtggaat tggtttaaca taacaaattg gctgtggtat ataaaattat tcataatgat    2040
agtaggaggc ttggtaggtt taagaatagt ttttgctgta ctttctatag tgaatagagt    2100
taggcaggga tattcaccat tatcgtttca gacccacctc ccaaccccga ggggacccga    2160
caggcccgaa ggaatagaag aagaaggtgg agagagagac agagacagat ccattcgatt    2220
agtgaacgga tctcgacggt atcggttatc cagggatcca ccggtatcca tgctagcgga    2280
tccgtcgact agggataaca gggtaattgt ttgaatgagg cttcagtact ttacagaatc    2340
gttgcctgca catcttggaa acacttgctg ggattacttc ttcaggttaa cccaacagaa    2400
ggctcgagaa ggtatattgc tgttgacagt gagcgagcaa gctgaccctg aagttcatct    2460
gtgaagccac agatgggatg aacttcaggg tcagcttgcc tgcctactgc ctcggaattc    2520
aaggggctac tttaggagca attatcttgt ttactaaaac tgaatacctt gctatctctt    2580
tgatacattt ttacaaagct gaattaaaat ggtataaatt aaactcgagg ctagcctgca    2640
gacgcgtgtt aacttttaaa agaaaagggg ggattggggg gtacagtgca ggggaaagaa    2700
tagtagacat aatagcaaca gacatacaaa ctaaagaatt acaaaaacaa attacaaaaa    2760
ttcaaaattt tgtcgacaat caacctctgg attacaaaat ttgtgaaaga ttgactggta    2820
ttcttaacta tgttgctcct tttacgctat gtggatacgc tgctttaatg cctttgtatc    2880
atgctattgc ttcccgtatg gctttcattt tctcctcctt gtataaatcc tggttgctgt    2940
ctctttatga ggagttgtgg cccgttgtca ggcaacgtgg cgtggtgtgc actgtgtttg    3000
ctgacgcaac ccccactggt tggggcattg ccaccacctg tcagctcctt tccgggactt    3060
tcgctttccc cctccctatt gccacggcgg aactcatcgc cgcctgcctt gcccgctgct    3120 ggacagggc tcggctgttg ggcactgaca attccgtggt gttgtcgggg aagctgacgt    3180
cctttccatg gctgctcgcc tgtgttgcca cctggattct gcgcgggacg tccttctgct    3240
acgtcccttc ggccctcaat ccagcggacc ttccttcccg cggcctgctg ccggctctgc    3300
ggcctcttcc gcgtcttcgc cttcgccctc agacgagtcg gatctccctt tgggccgcct    3360
ccccgcctgg gaattgatcc cgatggctcg ctcaacaaag ggtaaaattc tcttctgggg    3420
ttctggattt tcaccgacag atctctccga aaacctctgt actgttaagg tagcaaagga    3480
ccaaggccaa atgacgctga gatagtctca gcctgggtcc gagggtccag aggtcgctaa    3540
agaacgcgtg ctgcaaaggc gcacagcacc ttcggccccg gcccccagcc cgccgctgcc    3600
tcccctcccc cattccccct tctctttctt tcttctgggt cgctcgcccc accccgcggt    3660
tcctcacggc tcctgggcca atggtctcag ggccccggtg cacagcaact gatgggcacg    3720
gggttccagg cctaggccag ccaatcaggg cgcctggggg cgggcacaag ctgccaataa    3780
aaagtactga gcagcccgca accctccaca gccgagggat ccaagggtgg gcgcgccgac    3840
ccagctttct tgtacaaagt ggtgataatt cctgcagccc gggggatcca ctagttctag    3900
gatccaccat gtctagactg gacaagagca agtcataaa ctctgctctg gaattactca    3960
atgaagtcgg tatcgaaggc ctgacgacaa ggaaactcgc tcaaaagctg ggagttgagc    4020
agcctaccct gtactggcac gtgaagaaca gcgggccct gctcgatgcc ctggcaatcg    4080
agatgctgga caggcatcat acccacttct gccccctgga aggcgagtca tggcaagact    4140
ttctgcggaa caacgccaag tcattccgct gtgctctcct ctcacatcgc gacgggctaa    4200
aagtgcatct cggcacccgc ccaacagaga aacagtacga aaccctggaa aatcagctcg    4260
```

```
cgttcctgtg tcagcaaggc ttctccctgg agaacgcact gtacgctctg tccgccgtgg    4320
gccactttac actgggctgc gtattggagg atcaggagca tcaagtagca aaagaggaaa    4380
gagagacacc taccaccgat tctatgcccc cacttctgag acaagcaatt gagctgttcg    4440
accatcaggg agccgaacct gccttccttt tcggcctgga actaatcata tgtggcctgg    4500
agaaacagct aaagtgcgaa agcggcgggc cggccgacgc ccttgacgat tttgacttag    4560
acatgctccc agccgatgcc cttgacgact ttgaccttga tatgctgcct gctgacgctc    4620
ttgacgattt tgaccttgac atgctccccg ggtaactaag taaggatcga tatggcattc    4680
accgcgtgcc ttaattcgaa tggcattcac cgcgtgcctt aaacgcgttg cattcaccg     4740 cgtgccttaa atgcattggc attcaccgcg tgccttactg cagggtacct taattccgtt    4800
taagaccaat gacttacaag gcagctgtag atcttagcca cttttttaaaa gaaaagggg    4860 gactggaagg gctaattcac tcccaacgaa gacaagatat gatcccgggc tcgagtttac    4920
cactccctat cagtgataga gaaaagtgaa agtcgagttt accactccct atcagtgata    4980
gagaaaagtg aaagtcgagt ttaccactcc ctatcagtga tagagaaaag tgaaagtcga    5040
gtttaccact ccctatcagt gatagagaaa agtgaaagtc gagtttacca ctccctatca    5100
gtgatagaga aaagtgaaag tcgagtttac cactccctat cagtgataga gaaaagtgaa    5160
agtcgagttt accactccct atcagtgata gagaaaagtg aaagtcgagc tcggtacccg    5220
ggtcgagtag gcgttgatca gatgctgcat ataagcagct gcttttttgct tgtactgggt    5280 ctctctggtt agaccagatc tgagcctggg agctctctgg ctaactaggg aacccactgc    5340
ttaagcctca ataaagcttg ccttgagtgc ttcaagtagt gtgtgcccgt ctgttgtgtg    5400
actctggtaa ctagagatcc ctcagaccct tttagtcagt gtggaaaatc tctagca       5457
```

<210> SEQ ID NO 12  
<211> LENGTH: 8694  
<212> TYPE: DNA  
<213> ORGANISM: Artificial  
<220> FEATURE:  
<223> OTHER INFORMATION: Vector for inactivating the huntigtin gene specifically in astrocytes

<400> SEQUENCE: 12

```
aagcttggcc attgcatacg ttgtatccat atcataatat gtacatttat attggctcat      60
gtccaacatt accgccatgt tgacattgat tattgactag ttattaatag taatcaatta     120
cggggtcatt agttcatagc ccatatatgg agttccgcgt tacataactt acggtaaatg     180
gcccgcctgg ctgaccgccc aacgaccccc gcccattgac gtcaataatg acgtatgttc     240
ccatagtaac gccaataggg actttccatt gacgtcaatg ggtggagtat ttacggtaaa     300
ctgcccactt ggcagtacat caagtgtatc atatgccaag tacgccccct attgacgtca     360
atgacggtaa atggcccgcc tggcattatg cccagtacat gaccttatgg gactttccta     420
cttggcagta catctacgta ttagtcatcg ctattaccat ggtgatgcgg ttttggcagt     480
acatcaatgg gcgtggatag cggtttgact cacggggatt tccaagtctc cacccccattg    540 acgtcaatgg gagtttgttt tggcaccaaa atcaacggga ctttccaaaa tgtcgtaaca     600
actccgcccc attgacgcaa atgggcggta ggcgtgtacg gtgggaggtc tatataagca     660
gagctcgttt agtgaaccgg ggtctctctg gttagaccag atctgagcct gggagctctc     720
tggctaacta gggaacccac tgcttaagcc tcaataaagc ttgccttgag tgcttcaagt     780
agtgtgtgcc cgtctgttgt gtgactctgg taactagaga tccctcagac ccttttagtc     840
```

```
agtgtggaaa atctctagca gtggcgcccg aacagggacc tgaaagcgaa agggaaacca    900
gagctctctc gacgcaggac tcggcttgct gaagcgcgca cggcaagagg cgagggggcgg    960
cgactggtga gtacgccaaa aattttgact agcggaggct agaaggagag agatgggtgc   1020
gagagcgtca gtattaagcg ggggagaatt agatcgcgat gggaaaaaat tcggttaagg   1080
ccagggggaa agaaaaaata taaattaaaa catatagtat gggcaagcag ggagctagaa   1140
cgattcgcag ttaatcctgg cctgttagaa acatcagaag gctgtagaca aatactggga   1200
cagctacaac catcccttca gacaggatca gaagaactta gatcattata aatacagta   1260
gcaaccctct attgtgtgca tcaaggata gagataaaag acaccaagga agctttagac   1320
aagatagagg aagagcaaaa caaaagtaag accaccgcac agcaagcggc cgctgatctt   1380
cagacctgga ggaggagata tgagggacaa ttggagaagt gaattatata aatataaagt   1440
agtaaaaatt gaaccattag gagtagcacc caccaaggca aagagaagag tggtgcagag   1500
agaaaaaaga gcagtgggaa taggagcttt gttccttggg ttcttgggag cagcaggaag   1560
cactatgggc gcagcctcaa tgacgctgac ggtacaggcc agacaattat tgtctggtat   1620
agtgcagcag cagaacaatt tgctgagggc tattgaggcg caacagcatc tgttgcaact   1680
cacagtctgg ggcatcaagc agctccaggc aagaatcctg gctgtggaaa gatacctaaa   1740
ggatcaacag ctcctgggga tttggggttg ctctggaaaa ctcatttgca ccactgctgt   1800
gccttggaat gctagttgga gtaataaatc tctggaacag atttggaatc acacgacctg   1860
gatggagtgg gacagagaaa ttaacaatta cacaagctta atacactcct taattgaaga   1920
atcgcaaaac cagcaagaaa agaatgaaca agaattattg gaattagata atgggcaag   1980
tttgtggaat tggtttaaca taacaaattg gctgtggtat ataaaattat tcataatgat   2040
agtaggaggc ttggtaggtt taagaatagt ttttgctgta ctttctatag tgaatagagt   2100
taggcaggga tattcaccat tatcgtttca gacccacctc ccaaccccga ggggacccga   2160
caggcccgaa ggaatagaag aagaaggtgg agagagagac agagacagat ccattcgatt   2220
agtgaacgga tctcgacggt atcggttatc cagggatcca ccggtatcca tgctagcgga   2280
tccgtcgact agggataaca gggtaattgt ttgaatgagg cttcagtact ttacagaatc   2340
gttgcctgca catcttggaa acacttgctg ggattacttc ttcaggttaa cccaacagaa   2400
ggctcgagaa ggtatattgc tgttgacagt gagcgagcaa gctgaccctg aagttcatct   2460
gtgaagccac agatgggatg aacttcaggg tcagcttgcc tgcctactgc ctcggaattc   2520
aagggctac tttaggagca attatcttgt ttactaaaac tgaataccttt gctatctctt   2580
tgatacattt ttacaaagct gaattaaaat ggtataaatt aaactcgagg ctagcctgca   2640
gacgcgtgtt aactttttaaa agaaaagggg ggattggggg gtacagtgca ggggaaagaa   2700
tagtagacat aatagcaaca gacatacaaa ctaaagaatt acaaaaacaa attacaaaaaa   2760
ttcaaaatttt tgtcgacaat caacctctgg attacaaaat ttgtgaaaga ttgactggta   2820
ttcttaacta tgttgctcct tttacgctat gtggatacgc tgctttaatg cctttgtatc   2880
atgctattgc ttcccgtatg ctttcatttt tctcctcctt gtataaatcc tggttgctgt   2940
ctctttatga ggagttgtgg cccgttgtca ggcaacgtgg cgtggtgtgc actgtgtttg   3000
ctgacgcaac ccccactggt tggggcattg ccaccacctg tcagctcctt tccgggactt   3060
tcgctttccc cctccctatt gccacggcgg aactcatcgc cgcctgcctt gcccgctgct   3120
ggacaggggc tcggctgttg ggcactgaca attccgtggt gttgtcgggg aagctgacgt   3180
```

```
cctttccatg gctgctcgcc tgtgttgcca cctggattct gcgcgggacg tccttctgct   3240
acgtcccttc ggccctcaat ccagcggacc ttccttcccg cggcctgctg ccggctctgc   3300
ggcctcttcc gcgtcttcgc cttcgccctc agacgagtcg gatctcccct tgggccgcct   3360
ccccgcctgg gaattgatcc cgatggctcg ctcaacaaag ggtaaaattc tcttctgggg   3420
ttctggattt tcaccgacag atctctccga aaacctctgt actgttaagg tagcaaagga   3480
ccaaggccaa atgacgctga gatagtctca gcctgggtcc gagggtccag aggtcgctaa   3540
agaacgcgtg ctgcaaaggc gcacagcacc ttcggccccg gcccccagc cgccgctgcc    3600
tccccctcccc cattcccctt tctctttctt tcttctgggt cgctcgcccc accccgcggt  3660
tcctcacggc tcctgggcca atggtctcag ggccccggtg cacagcaact gatgggcacg   3720
gggttccagg cctaggccag ccaatcaggg cgcctggggg cggcacaag ctgccaataa    3780
aaagtactga gcagcccgca accctccaca gccgagggat ccaagggtgg gcgcgccgac   3840
ccagctttct tgtacaaagt ggtgataatt cctgcagccc gggggatcca ctagttctag   3900
gatccaccat gtctagactg gacaagagca aagtcataaa ctctgctctg gaattactca   3960
atgaagtcgg tatcgaaggc ctgacgacaa ggaaactcgc tcaaaagctg ggagttgagc   4020
agcctaccct gtactggcac gtgaagaaca agcgggccct gctcgatgcc ctggcaatcg   4080
agatgctgga caggcatcat acccacttct gcccccctgga aggcgagtca tggcaagact  4140
ttctgcggaa caacgccaag tcattccgct gtgctctcct ctcacatcgc gacggggcta   4200
aagtgcatct cggcacccgc ccaacagaga aacagtacga aaccctggaa aatcagctcg   4260
cgttcctgtg tcagcaaggc ttctcccctgg agaacgcact gtacgctctg tccgccgtgg  4320
gccactttac actgggctgc gtattggagg atcaggagca tcaagtagca aagaggaaa    4380
gagagacacc taccaccgat tctatgcccc cacttctgag acaagcaatt gagctgttcg   4440
accatcaggg agccgaacct gccttccttt tcggcctgga actaatcata tgtggcctgg   4500
agaaacagct aaagtgcgaa agcggcgggc cggccgacgc ccttgacgat tttgacttag   4560
acatgctccc agccgatgcc cttgacgact ttgaccttga tatgctgcct gctgacgctc   4620
ttgacgattt tgaccttgac atgctccccg ggtaactaag taaggatcga tatggcattc   4680
accgcgtgcc ttaattcgaa tggcattcac cgcgtgcctt aaacgcgttg gcattcaccg   4740
cgtgccttaa atgcattggc attcaccgcg tgccttactg cagggtacct taattccgtt   4800
taagaccaat gacttacaag gcagctgtag atcttagcca ctttttaaaa gaaaaggggg   4860
gactggaagg gctaattcac tcccaacgaa gacaagatat gatcccgggc tcgagtttac   4920
cactccctat cagtgataga gaaaagtgaa agtcgagttt accactccct atcagtgata   4980
gagaaaagtg aaagtcgagt ttaccactcc ctatcagtga tagagaaaag tgaaagtcga   5040
gtttaccact ccctatcagt gatagagaaa agtgaaagtc gagtttacca ctccctatca   5100
gtgatagaga aaagtgaaag tcgagtttac cactccctat cagtgataga gaaaagtgaa   5160
agtcgagttt accactccct atcagtgata gagaaaagtg aaagtcgagc tcggtacccg   5220
ggtcgagtag gcgttgatca gatgctgcat ataagcagct gcttttttgct tgtactgggt  5280
ctctctggtt agaccagatc tgagcctggg agctctctgg ctaactaggg aacccactgc   5340
ttaagcctca ataaagcttg ccttgagtgc ttcaagtagt gtgtgcccgt ctgttgtgtg   5400
actctggtaa ctagagatcc ctcagaccct tttagtcagt gtggaaaatc tctagcagta   5460
gtagttcatg tcatcttatt attcagtatt tataacttgc aaagaaatga atatcagaga   5520
gtgagaggaa cttgtttatt gcagcttata atggttacaa ataaagcaat agcatcacaa   5580
```

```
atttcacaaa taaagcattt ttttcactgc attctagttg tggtttgtcc aaactcatca   5640
atgtatctta tcatgtctgg ctctagctat cccgcccta actccgccca gttccgccca    5700
ttctccgccc catggctgac taattttttt tatttatgca gaggccgagg ccgcctcggc   5760
ctctgagcta ttccagaagt agtgaggagg cttttttgga ggcctaggct tttgcgtcga   5820
gacgtaccca attcgcccta tagtgagtcg tattacgcgc gctcactggc cgtcgtttta   5880
caacgtcgtg actgggaaaa ccctggcgtt acccaactta atcgccttgc agcacatccc   5940
cctttcgcca gctggcgtaa tagcgaagag gcccgcaccg atcgcccttc ccaacagttg   6000
cgcagcctga atggcgaatg gcgcgacgcg cctgtagcg gcgcattaag cgcggcgggt    6060
gtggtggtta cgcgcagcgt gaccgctaca cttgccagcg ccctagcgcc cgctcctttc   6120
gctttcttcc cttcctttct cgccacgttc gccggctttc cccgtcaagc tctaaatcgg   6180
gggctccctt tagggttccg atttagtgct ttacggcacc tcgaccccaa aaaacttgat   6240
tagggtgatg gttcacgtag tgggccatcg ccctgataga cggttttcg ccctttgacg    6300
ttggagtcca cgttctttaa tagtggactc ttgttccaaa ctggaacaac actcaaccct   6360
atctcggtct attcttttga tttataaggg attttgccga tttcggccta ttggttaaaa   6420
aatgagctga tttaacaaaa atttaacgcg aattttaaca aaatattaac gtttacaatt   6480
tcccaggtgg cacttttcgg ggaaatgtgc gcggaacccc tatttgttta ttttctaaa    6540
tacattcaaa tatgtatccg ctcatgagac aataaccctg ataaatgctt caataatatt   6600
gaaaaaggaa gagtatgagt attcaacatt tccgtgtcgc ccttattccc ttttttgcgg   6660
cattttgcct tcctgttttt gctcacccag aaacgctggt gaaagtaaaa gatgctgaag   6720
atcagttggg tgcacgagtg ggttacatcg aactggatct caacagcggt aagatccttg   6780
agagttttcg ccccgaagaa cgttttccaa tgatgagcac ttttaaagtt ctgctatgtg   6840
gcgcggtatt atcccgtatt gacgccgggc aagagcaact cggtcgccgc atacactatt   6900
ctcagaatga cttggttgag tactcaccag tcacagaaaa gcatcttacg gatggcatga   6960
cagtaagaga attatgcagt gctgccataa ccatgagtga taacactgcg gccaacttac   7020
ttctgacaac gatcggagga ccgaaggagc taaccgcttt tttgcacaac atggggatc    7080
atgtaactcg ccttgatcgt tgggaaccgg agctgaatga agccatacca aacgacgagc   7140
gtgacaccac gatgcctgta gcaatggcaa caacgttgcg caaactatta actggcgaac   7200
tacttactct agcttcccgg caacaattaa tagactggat ggaggcggat aaagttgcag   7260
gaccacttct gcgctcggcc cttccggctg gctggtttat tgctgataaa tctggagccg   7320
gtgagcgtgg gtctcgcggt atcattgcag cactggggcc agatggtaag ccctcccgta   7380
tcgtagttat ctacacgacg gggagtcagg caactatgga tgaacgaaat agacagatcg   7440
ctgagatagg tgcctcactg attaagcatt ggtaactgtc agaccaagtt tactcatata   7500
tactttagat tgatttaaaa cttcatttt aatttaaaag gatctaggtg aagatccttt    7560
ttgataatct catgaccaaa atcccttaac gtgagttttc gttccactga gcgtcagacc   7620
ccgtagaaaa gatcaaagga tcttcttgag atcctttttt tctgcgcgta atctgctgct   7680
tgcaaacaaa aaaaccaccg ctaccagcgg tggtttgttt gccggatcaa gagctaccaa   7740
ctcttttttcc gaaggtaact ggcttcagca gagcgcagat accaaatact gtccttctag   7800
tgtagccgta gttaggccac cacttcaaga actctgtagc accgcctaca tacctcgctc   7860
tgctaatcct gttaccagtg gctgctgcca gtggcgataa gtcgtgtctt accgggttgg   7920
```

```
actcaagacg atagttaccg gataaggcgc agcggtcggg ctgaacgggg ggttcgtgca    7980
cacagcccag cttggagcga acgacctaca ccgaactgag atacctacag cgtgagctat    8040
gagaaagcgc cacgcttccc gaagggagaa aggcggacag gtatccggta agcggcaggg    8100
tcggaacagg agagcgcacg agggagcttc caggggggaaa cgcctggtat ctttatagtc    8160
ctgtcgggtt tcgccacctc tgacttgagc gtcgattttt gtgatgctcg tcagggggc     8220 ggagcctatg gaaaaacgcc agcaacgcgg ccttttttacg gttcctggcc ttttgctggc    8280
cttttgctca catgttcttt cctgcgttat cccctgattc tgtggataac cgtattaccg    8340
cctttgagtg agctgatacc gctcgccgca gccgaacgac cgagcgcagc gagtcagtga    8400
gcgaggaagc ggaagagcgc ccaatacgca aaccgcctct ccccgcgcgt tggccgattc    8460
attaatgcag ctggcacgac aggtttcccg actggaaagc gggcagtgag cgcaacgcaa    8520
ttaatgtgag ttagctcact cattaggcac cccaggcttt acactttatg cttccggctc    8580
gtatgttgtg tggaattgtg agcggataac aatttcacac aggaaacagc tatgaccatg    8640
attacgccaa gcgcgcaatt aaccctcact aaagggaaca aaagctggag ctgc           8694
```

<210> SEQ ID NO 13
<211> LENGTH: 5406
<212> TYPE: DNA
<213> ORGANISM: Artificial
<220> FEATURE:
<223> OTHER INFORMATION: Vector for the inactivation of genes
      specifically in astrocytes

<400> SEQUENCE: 13

```
aagcttggcc attgcatacg ttgtatccat atcataatat gtacatttat attggctcat      60
gtccaacatt accgccatgt tgacattgat tattgactag ttattaatag taatcaatta    120
cggggtcatt agttcatagc ccatatatgg agttccgcgt tacataactt acggtaaatg    180
gcccgcctgg ctgaccgccc aacgaccccc gcccattgac gtcaataatg acgtatgttc    240
ccatagtaac gccaataggg actttccatt gacgtcaatg ggtggagtat ttacggtaaa    300
ctgcccactt ggcagtacat caagtgtatc atatgccaag tacgccccct attgacgtca    360
atgacggtaa atggcccgcc tggcattatg cccagtacat gaccttatgg gactttccta    420
cttggcagta catctacgta ttagtcatcg ctattaccat ggtgatgcgg ttttggcagt    480
acatcaatgg gcgtggatag cggtttgact cacggggatt tccaagtctc cacccccattg    540 acgtcaatgg gagtttgttt tggcaccaaa atcaacggga ctttccaaaa tgtcgtaaca    600
actccgcccc attgacgcaa atgggcggta ggcgtgtacg gtgggaggtc tatataagca    660
gagctcgttt agtgaaccgg ggtctctctg gttagaccag atctgagcct gggagctctc    720
tggctaacta gggaacccac tgcttaagcc tcaataaagc ttgccttgag tgcttcaagt    780
agtgtgtgcc cgtctgttgt gtgactctgg taactagaga tccctcagac ccttttagtc    840
agtgtggaaa atctctagca gtggcgcccg aacaggg acc tgaaagcgaa agggaaacca    900
gagctctctc gacgcaggac tcggcttgct gaagcgcgca cggcaagagg cgaggggcgg    960
cgactggtga gtacgccaaa aattttgact agcggaggct agaaggagag agatgggtgc   1020
gagagcgtca gtattaagcg ggggagaatt agatcgcgat gggaaaaaat tcggttaagg   1080
ccagggggaa agaaaaaata taaattaaaa catatagtat gggcaagcag ggagctagaa   1140
cgattcgcag ttaatcctgg cctgttagaa acatcagaag gctgtagaca atactggga    1200 cagctacaac catcccttca gacaggatca gaagaactta gatcattata taatacagta   1260
```

```
gcaaccctct attgtgtgca tcaaaggata gagataaaag acaccaagga agctttagac       1320
aagatagagg aagagcaaaa caaaagtaag accaccgcac agcaagcggc cgctgatctt       1380
cagacctgga ggaggagata tgagggacaa ttggagaagt gaattatata aatataaagt       1440
agtaaaaatt gaaccattag gagtagcacc caccaaggca agagaagag tggtgcagag        1500 agaaaaaaga gcagtgggaa taggagcttt gttccttggg ttcttgggag cagcaggaag       1560
cactatgggc gcagcctcaa tgacgctgac ggtacaggcc agacaattat tgtctggtat       1620
agtgcagcag cagaacaatt tgctgagggc tattgaggcg caacagcatc tgttgcaact       1680
cacagtctgg ggcatcaagc agctccaggc aagaatcctg gctgtggaaa gatacctaaa       1740
ggatcaacag ctcctgggga tttggggttg ctctggaaaa ctcatttgca ccactgctgt       1800
gccttggaat gctagttgga gtaataaatc tctggaacag atttggaatc acacgacctg       1860
gatggagtgg gacagagaaa ttaacaatta cacaagctta atacactcct taattgaaga       1920
atcgcaaaac cagcaagaaa agaatgaaca agaattattg gaattagata aatgggcaag       1980
tttgtggaat tggtttaaca taacaaattg gctgtggtat ataaaattat tcataatgat       2040
agtaggaggc ttggtaggtt taagaatagt ttttgctgta ctttctatag tgaatagagt       2100
taggcaggga tattcaccat tatcgtttca gacccacctc ccaaccccga ggggacccga       2160
caggcccgaa ggaatagaag aagaaggtgg agagagagac agagacagat ccattcgatt       2220
agtgaacgga tctcgacggt atcggttatc cagggatcca ccggtatcca tgctagcgga       2280
tccgtcgact agggataaca gggtaattgt ttgaatgagg cttcagtact ttacagaatc       2340
gttgcctgca catcttggaa acacttgctg ggattacttc ttcaggttaa cccaacagaa       2400
ggctcgagaa ggtatattgc tgttgacagt gagcgatatc gcatgcgcct gcctactgcc       2460
tcggaattca aggggctact ttaggagcaa ttatcttgtt tactaaaact gaataccttg       2520
ctatctcttt gatacatttt tacaaagctg aattaaaatg gtataaatta aactcgaggc       2580
tagcctgcag acgcgtgtta actttttaaa gaaaaggggg gattgggggg tacagtgcag       2640
gggaaagaat agtagacata atagcaacag acatacaaac taaagaatta caaaaacaaa       2700
ttacaaaaat tcaaaatttt gtcgacaatc aacctctgga ttacaaaatt tgtgaaagat       2760
tgactggtat tcttaactat gttgctcctt ttacgctatg tggatacgct gctttaatgc       2820
ctttgtatca tgctattgct tcccgtatgg ctttcatttt ctcctccttg tataaatcct       2880
ggttgctgtc tctttatgag gagttgtggc ccgttgtcag gcaacgtggc gtggtgtgca       2940
ctgtgtttgc tgacgcaacc cccactggtt ggggcattgc caccacctgt cagctccttt       3000
ccgggacttt cgctttcccc ctccctattg ccacggcgga actcatcgcc gcctgccttg       3060
cccgctgctg acaggggct cggctgttgg gcactgacaa ttccgtggtg ttgtcgggga       3120
agctgacgtc ctttccatgg ctgctcgcct gtgttgccac ctggattctg cgcgggacgt       3180
ccttctgcta cgtcccttcg gccctcaatc cagcggacct tccttcccgc ggcctgctgc       3240
cggctctgcg gcctcttccg cgtcttcgcc ttcgccctca gacgagtcgg atctcccttt       3300
gggccgcctc cccgcctggg aattgatccc gatggctcgc tcaacaaagg gtaaaattct       3360
cttctggggt tctggatttt caccgacaga tctctccgaa aacctctgta ctgttaaggt       3420
agcaaaggac caaggccaaa tgacgctgag atagtctcag cctgggtccg agggtccaga       3480
ggtcgctaaa gaacgcgtgc tgcaaaggcg cacagcacct tcggcccgg cccccagcc         3540 gccgctgcct cccctccccc attccccttt ctctttcttt cttctgggtc gctcgcccca       3600
ccccgcggtt cctcacggct cctgggccaa tggtctcagg gccccggtgc acagcaactg       3660
```

```
atgggcacgg ggttccaggc ctaggccagc caatcagggc gcctgggggc gggcacaagc    3720
tgccaataaa aagtactgag cagcccgcaa ccctccacag ccgagggatc caagggtggg    3780
cgcgccgacc cagctttctt gtacaaagtg gtgataattc ctgcagcccg ggggatccac    3840
tagttctagg atccaccatg tctagactgg acaagagcaa agtcataaac tctgctctgg    3900
aattactcaa tgaagtcggt atcgaaggcc tgacgacaag gaaactcgct caaaagctgg    3960
gagttgagca gcctaccctg tactggcacg tgaagaacaa gcgggccctg ctcgatgccc    4020
tggcaatcga gatgctggac aggcatcata cccacttctg ccccctggaa ggcgagtcat    4080
ggcaagactt tctgcggaac aacgccaagt cattccgctg tgctctcctc tcacatcgcg    4140
acggggctaa agtgcatctc ggcacccgcc aacagagaa acagtacgaa accctggaaa    4200
atcagctcgc gttcctgtgt cagcaaggct ctcccctgga gaacgcactg tacgctctgt    4260
ccgccgtggg ccactttaca ctgggctgcg tattggagga tcaggagcat caagtagcaa    4320
aagaggaaag agagacacct accaccgatt ctatgccccc acttctgaga caagcaattg    4380
agctgttcga ccatcaggga gccgaacctg ccttcctttt cggcctggaa ctaatcatat    4440
gtggcctgga gaaacagcta aagtgcgaaa gcggcgggcc ggccgacgcc cttgacgatt    4500
ttgacttaga catgctccca gccgatgccc ttgacgactt tgaccttgat atgctgcctg    4560
ctgacgctct tgacgatttt gaccttgaca tgctccccgg gtaactaagt aaggatcgat    4620
atggcattca ccgcgtgcct taattcgaat ggcattcacc gcgtgcctta acgcgttgg    4680
cattcaccgc gtgccttaaa tgcattgca ttcaccgcgt gccttactgc agggtacctt    4740
aattccgttt aagaccaatg acttacaagg cagctgtaga tcttagccac ttttaaaag    4800
aaaaggggg actggaaggg ctaattcact cccaacgaag acaagatatg atcccgggct    4860
cgagtttacc actccctatc agtgatagag aaaagtgaaa gtcgagttta ccactcccta    4920
tcagtgatag agaaaagtga agtcgagtt taccactccc tatcagtgat agagaaaagt    4980
gaaagtcgag tttaccactc cctatcagtg atagagaaaa gtgaaagtcg agtttaccac    5040
tccctatcag tgatagagaa aagtgaaagt cgagtttacc actccctatc agtgatagag    5100
aaaagtgaaa gtcgagttta ccactcccta tcagtgatag agaaaagtga aagtcgagct    5160
cggtacccgg gtcgagtagg cgttgatcag atgctgcata taagcagctg ctttttgctt    5220
gtactgggtc tctctggtta gaccagatct gagcctggga gctctctggc taactaggga    5280
acccactgct taagcctcaa taaagcttgc cttgagtgct tcaagtagtg tgtgcccgtc    5340
tgttgtgtga ctctggtaac tagagatccc tcagaccctt ttagtcagtg tggaaaatct    5400
ctagca                                                               5406
```

<210> SEQ ID NO 14
<211> LENGTH: 21
<212> TYPE: RNA
<213> ORGANISM: Homo sapiens

<400> SEQUENCE: 14
uaaggcacgc ggugaaugcc a    21

<210> SEQ ID NO 15
<211> LENGTH: 31
<212> TYPE: DNA
<213> ORGANISM: Artificial sequence
<220> FEATURE:
<223> OTHER INFORMATION: PCR primer -continued

<400> SEQUENCE: 15
caccatcgat ggctcgctca acaaagggta a 31

<210> SEQ ID NO 16
<211> LENGTH: 27
<212> TYPE: DNA
<213> ORGANISM: Artificial sequence
<220> FEATURE:
<223> OTHER INFORMATION: PCR primer

<400> SEQUENCE: 16
ggatccctcg gctgtggagg gttgcgg 27

<210> SEQ ID NO 17
<211> LENGTH: 23
<212> TYPE: RNA
<213> ORGANISM: Homo sapiens

<400> SEQUENCE: 17
ucuuugguua ucuagcugua uga 23

<210> SEQ ID NO 18
<211> LENGTH: 23
<212> TYPE: DNA
<213> ORGANISM: Artificial sequence
<220> FEATURE:
<223> OTHER INFORMATION: miR9 target coding sequence (miR9T)

<400> SEQUENCE: 18
agaaaccaat agatcgacat act 23

<210> SEQ ID NO 19
<211> LENGTH: 23
<212> TYPE: DNA
<213> ORGANISM: Artificial sequence
<220> FEATURE:
<223> OTHER INFORMATION: miR9 target coding sequence (miR9T)

<400> SEQUENCE: 19
tcatacagct agataaccaa aga 23